US011311533B2

(12) United States Patent
He

(10) Patent No.: US 11,311,533 B2
(45) Date of Patent: Apr. 26, 2022

(54) OPIOID RECEPTOR ANTAGONIST CONJUGATE AND USE THEREOF

(71) Applicant: SHANGHAI HANMAI BIO-PHARMA CO., LTD., Shanghai (CN)

(72) Inventor: Mei He, Shanghai (CN)

(73) Assignee: SHANGHAI HANMAI BIO-PHARMA CO., LTD., Shanghai (CN)

( * ) Notice: Subject to any disclaimer, the term of this patent is extended or adjusted under 35 U.S.C. 154(b) by 756 days.

(21) Appl. No.: 16/074,268

(22) PCT Filed: Jan. 26, 2017

(86) PCT No.: PCT/CN2017/072727
§ 371 (c)(1),
(2) Date: Jul. 31, 2018

(87) PCT Pub. No.: WO2017/133634
PCT Pub. Date: Aug. 10, 2017

(65) Prior Publication Data
US 2021/0121455 A1   Apr. 29, 2021

(30) Foreign Application Priority Data

Feb. 2, 2016 (CN) .......................... 201610072859.2

(51) Int. Cl.
| | | |
|---|---|---|
| A61K 31/485 | (2006.01) | |
| A61K 47/60 | (2017.01) | |
| A61P 1/10 | (2006.01) | |
| A61P 23/00 | (2006.01) | |
| A61K 31/439 | (2006.01) | |
| C07D 489/08 | (2006.01) | |

(52) U.S. Cl.
CPC .......... *A61K 31/485* (2013.01); *A61K 31/439* (2013.01); *A61K 47/60* (2017.08); *A61P 1/10* (2018.01); *A61P 23/00* (2018.01); *C07D 489/08* (2013.01)

(58) Field of Classification Search
CPC ..... C07D 489/08; A61K 31/485; A61K 47/60
See application file for complete search history.

(56) References Cited

U.S. PATENT DOCUMENTS

| | | |
|---|---|---|
| 2003/0022876 A1 | 1/2003 | Ashton et al. |
| 2003/0124086 A1 | 7/2003 | Bentley et al. |
| 2005/0136031 A1 | 6/2005 | Bentley et al. |
| 2010/0048602 A1 | 2/2010 | Riggs-Sauthier et al. |
| 2011/0160239 A1 | 6/2011 | Brodbeck et al. |
| 2011/0237614 A1 | 9/2011 | Jude-Fishburn et al. |
| 2013/0023553 A1 | 1/2013 | Jude-Fishburn et al. |
| 2014/0336214 A1 | 11/2014 | Riley et al. |
| 2015/0038524 A1 | 2/2015 | Aslund et al. |
| 2015/0045555 A1 | 2/2015 | Guo et al. |
| 2016/0136153 A1 | 5/2016 | Jenkins |

FOREIGN PATENT DOCUMENTS

| | | |
|---|---|---|
| CN | 1514729 A | 7/2004 |
| CN | 101646464 A | 2/2010 |
| CN | 102159249 A | 8/2011 |
| CN | 102573918 A | 7/2012 |
| CN | 103237547 A | 8/2013 |
| CN | 103289075 A | 9/2013 |
| CN | 104473927 A | 4/2015 |
| EP | 2628489 A1 | 8/2013 |
| JP | 2007-514761 A | 6/2007 |
| JP | 2010-521466 A | 6/2010 |
| JP | 2014-532728 A | 12/2014 |
| WO | WO 03/032990 A2 | 4/2003 |
| WO | WO 2005/058367 A2 | 6/2005 |
| WO | WO 2008/112288 A2 | 9/2008 |
| WO | WO 2011/088140 A1 | 7/2011 |
| WO | WO 2016/064914 A1 | 4/2016 |

OTHER PUBLICATIONS

Johansson (Journal of Chromatography B, 1994, 652, 137-147 (Year: 1994).*
Brock. Drugs, 2012, 72(14), 1947-1865 (Year: 2012).*
Erez et al., "Narcotic Antagonistic Potency of Bivalent Ligands Which Contain β-Naltrexamine. Evidence for Bridging between Proximal Recognition Sites", J. Med. Chem., 1982, 25, 847-849.
Neumann et al., "Evaluation of Single Oral Doses of NKTR-118 (Pegnaloxol) as a Peripheral Opioid Antagonist (POA): A Double-Blind Placebo-Controlled Study in Healthy Male Subjects", J. Clin. Pharmacol., 2007, 2 pages.
Portoghese et al., "Tena, A Selective Kappa Opioid Receptor Antagonist", Life Sciences, 1984, vol. 36, 801-805.
Yerramreddy et al., "Novel 3-O-pegylated carboxylate and 3-O-pegylated carbamate prodrugs of naltrexone for microneedle-enhanced transdermal delivery", Bioorganic & Medicinal Chemistry Letters, 2010, 20, 3280-3283.

\* cited by examiner

*Primary Examiner* — Noble E Jarrell
(74) *Attorney, Agent, or Firm* — BakerHostetler

(57) ABSTRACT

The present invention relates to an opioid receptor antagonist conjugate and a use thereof. In particular, the present invention relates to a covalent coupling conjugate of a hydrophilic polymer and an opioid receptor antagonist and the use thereof.

12 Claims, 1 Drawing Sheet

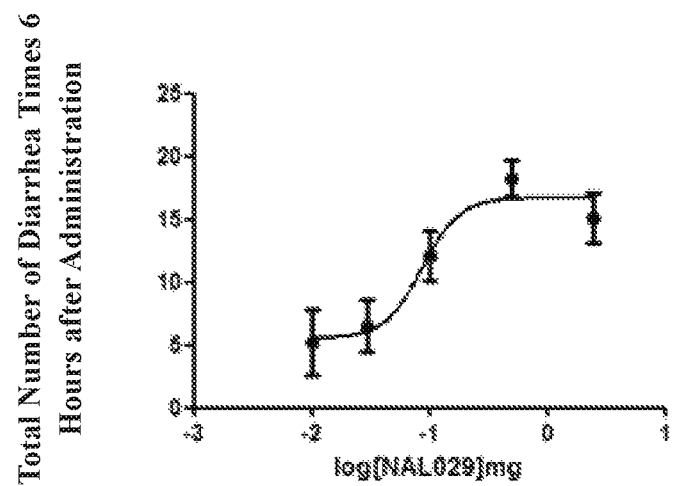

OPIOID RECEPTOR ANTAGONIST CONJUGATE AND USE THEREOF

CROSS REFERENCE TO RELATED APPLICATIONS

This application is a 371 National Stage Application of PCT/CN2017/072727 filed Jan. 26, 2017, which claims the priority to Chinese Patent Application No. 201610072859.2, titled "OPIOID RECEPTOR ANTAGONIST CONJUGATE AND USE THEREOF", filed with State Intellectual Property Office of People's Republic of China on Feb. 2, 2016, and the disclosures of which are hereby incorporated by reference.

FIELD

The present disclosure relates to an opioid receptor antagonist conjugate and a use thereof. In particular, the present disclosure relates to a covalent coupling conjugate of a hydrophilic polymer and an opioid receptor antagonist and use thereof.

BACKGROUND

Body pain is one of the most common pains humans suffer from and also one of the most unbearable symptoms to patients. Just for cancer pain, at least 5 million cancer patients suffer from pain every day according to statistics. There are 1.8 million new cancer cases and nearly 1.4 million deaths from cancer occurring in China every year. Among these patients, 50% of them have moderate to severe pain, wherein 30% is unbearable severe pain. By 2020, 20 million new cancer cases and 16 million deaths from cancer are projected to occur in the world, 70% of which will distribute in developing countries. In developing countries, however, most of the patients who seek medical attention have advanced cancers, and the prevalence of pain in advanced cancer patients is as high as 75% or more. The harm caused by cancer pain to cancer patients, families and society is enormous.

Opioids are the oldest analgesics and so far the most effective analgesic. Opioid analgesics have a strong pain-relieving effect; there is no organ toxicity in long-term drug treatment; the analgesic treatment effect can be improved by increasing the dose of the drug when patient's pain aggravated by the progression of the tumor. WHO proposed in 2000 that "opioid analgesics have an irreplaceable status for patients with moderate and severe cancer pain."

Currently, opioids are the most important drugs for the treatment of moderate and severe pain. However, such drugs may induce many adverse reactions such as nausea, vomiting, and drowsiness. But the above-mentioned adverse reactions are usually tolerated by most patients within one week; even the relatively severe hypoventilation is easily tolerated by patients, except for constipation, which is not only with a prevalence of 90% to 100%, but also the least tolerated.

The characteristics of the constipation caused by opioids are that patients will not built tolerances for constipation of opioids because of continuous medications, the constipation not only occurs in the early stage of medication, but also persistently exists in the whole process of opioid analgesic treatment. Constipation may induce serious complications and become the major barrier to effective pain relief if not timely controlled. At the same time, constipation may seriously affect the treatment of the disease, interrupt the treatment, greatly increase the length of patient's hospital stay, and seriously affect patient's life quality. Therefore, the prevention and treatment of constipation adverse reactions has always been a problem that cannot be ignored in opioid analgesic treatment period.

The earliest published constipation evaluation criteria include the following eight characteristic symptoms: abdominal distension, bloating; decreased gas pass; decreased number of intestinal peristalsis; overflowing of watery stools; rectal fullness and compression; rectal pain during intestinal peristalsis; decreased volume of stools; feeling of incomplete bowel movements and tenesmus (McMillan S C, Williams F A. 1989). Clinically, however, the commonly used evaluation criteria are: defecation strain; decreased number of bowel movements; decreased volume of stools and lumpy stools. Opioids induce functional bowel disorders by the following mechanisms (Galligan J J, Vanner S. 2005): 1) opioids bind to opioid receptors in intestinal tract to make intestinal peristalsis slow, intestinal fluid secretions decrease but absorption increase; 2) reduce excitability in the myenteric plexus and inhibit the activity of neurons; 3) increase muscle tone of smooth muscle in the intestinal wall and inhibit coordinated peristalsis such that it makes non-peristaltic contraction increase. Since human body's tolerance to the intestinal effects of opioids builds up very slow, the functional bowel disorders will persistently exist during treatment.

The general preventive measures for constipation are: when start taking opioids, patients should increase their fluid intake, increase their activity level or go on a cellulose-containing diet, develop and maintain a habit of regular bowel movements, and combining with a quiet defecation environment and sufficient time. However, these measures have limited effects on patients taking opioids daily and the best method is to use appropriate medications while using these measures.

In the treatment of constipation, there are using laxatives, choosing appropriate opioids and opioid antagonists to relieve or treat constipation induced by long-term use of opioid analgesics; the use of a single laxative is usually ineffective and requires routine use of irritating laxatives, however the effects of laxatives are not only non-specific, but also unpredictable, and often induce diarrhea and cramps. In addition, some patients in clinical practice still have constipation even if they use large amounts of laxatives. Since different opioids have different ratios of drug distribution in the central nervous system and gastrointestinal tracts, resulting in different severities of constipation, thus, choosing an appropriate opioid analgesic is also a way, to avoid or relieve constipation. It becomes a goal people pursued to find a drug that can block peripheral μ receptor without affecting the central analgesic effect of opioids. The opioid receptor antagonist itself has no agonistic effect on the opioid receptor but has a strong affinity for the μ receptor and certain affinities for the κ receptor, δ receptor and σ receptor, and can remove opioid analgesic drugs that bind to these receptors, thereby producing an antagonistic effect. Current research indicates that opioid receptors are not only found in the central nervous system which includes the brain and spinal cord, but also widely found in peripheral nerves and other parts. Systemic use of general opioid receptor antagonists has effects on both central and peripheral opioid receptors, which also attenuating central analgesic effects while antagonizing the peripheral effects of opioids, such as naloxone, naltrexone, and nalmefene.

Therefore, there is a demand of an opioid receptor antagonists which reduces toxic and side effects to the central nervous system without affecting the analgesic effects of opioids at the same time.

The PEGylation modification technique is a technique in which a polyethylene glycol derivative is linked to surface of a drug molecule to change a part of the properties of the drug molecule, Currently, NKTR-102 and NKTR-118 of Nektar are representative drugs of PEGylated small molecule drugs in domestic and abroad clinical and marketing.

SUMMARY

The inventors have surprisingly found that an opioid receptor antagonist modified by a hydrophilic polymer (e.g., polyethylene glycol) can significantly improve its tissue distribution in vivo, that is, there is almost no influence on the central nervous system but the peripheral system, thereby reducing the toxic and side effects of opioid receptor antagonists on the central nervous system, providing diverse and flexible treatment options for clinical applications.

Particularly, the inventors have also surprisingly found that compared with the conjugates of PEG and naloxone, the opioid receptor antagonists of the conjugates of PEG and naltrexone exhibit a higher activity and a lower ratio to pass through the blood-brain barrier. More particularly, the inventors have also surprisingly found that it is harder for double opioid receptor antagonist conjugates to pass through the blood brain barrier compared with mono opioid receptor antagonist conjugates, therefore they can target at the peripheral nervous system better without affecting the analgesic effect of the opioid but at the same time antagonizing the side effects of the opioid better.

In one aspect, the present disclosure provides a conjugate as represented by formula (I) and a pharmaceutically acceptable salt thereof:

P—(W)m    (I)

wherein, P is a hydrophilic polymer;
W is a non-naloxone opioid receptor antagonist;
m is a natural number between 1 and 10.

In some embodiments, the hydrophilic polymer is polyethylene glycol.

In some embodiments, the hydrophilic polymer is a polyethylene glycol having 2 to 45 —CH$_2$CH$_2$O— structural unit. Preferably, the number of —CH$_2$CH$_2$O— structural unit of the polyethylene glycol is 2, 3, 4, 5, 6, 7, 8, 9, 10, 15, 20, 25, 30, 35, 40 or any value between 2 and 45.

In some embodiments, the polyethylene glycol is a monodisperse polyethylene glycol.

In some embodiments, the non-naloxone opioid receptor antagonist is derived from compounds selected from the group consisting of: 6-amino-14-hydroxy-17-allyl norfloxacin morphine, naltrel, naltrexone, N-methylnaltrexone, nalmefene, nalbuphine, butorphanol, cyclazocine, pentazocine, nalorphine, naltrindole, nobelnatofimin, oxalin, letromorphin, methyl naltrexone, buprenorphine, seklowan, oxymorphone, codeine, oxycontin, morphine, ethylmorphine hydrochloride, diacetylmorphine, hydromorphone, dihydrocodeine, dihydromorphine and methamethorphan. In particular, the non-naloxone opioid receptor antagonist is derived from naltrexone, N-methylnaltrexone, nalmefene or nalbuphine.

In other embodiments, the non-naloxone opioid receptor antagonist is selected from activated forms or derived forms thereof from the following compounds: 6-amino-14-hydroxy-17-allyl norfloxacin morphine, naltrel, naltrexone, N-methylnaltrexone, nalmefene, nalbuphine, butorphanol, cyclozocine, pentazocine, nalorphine, naltrindole, nobelnatofimin, oxilorphan, levallorphan, methylnaltrexone, buprenorphine, seklowan, oxymorphone, codeine, oxycontin, morphine, ethylmorphine hydrochloride, diacetylmorphine, hydromorphone, dihydrocodeine, dihydromorphine and metformin. Particularly, the non-naloxone opioid receptor antagonist is an activated form of naltrexone, N-methylnaltrexone, nalmefene or nalbuphine. The terms "activated form" or "derived form" (which are used interchangeably) as used herein, refers to that, in order to be covalently bonded to a hydrophilic polymer, the modified form of an opioid receptor antagonist compound of the invention. Preferably, the activated forms substantially retain the activity of the opioid receptor antagonist.

In other embodiments, prior to conjugating with the hydrophilic polymer, the non-naloxone opioid receptor antagonist is selected from the group consisting of: 6-amino-14-hydroxy-17-allyl norfloxacin morphine, naltrel, naltrexone, N-methylnaltrexone, nalmefene, nalbuphine, butorphanol, cyclozocine, pentazocine, nalorphine, nobelnatofimin, oxilorphan, levallorphan, methylnaltrexone, buprenorphine, seklowan, oxymorphone, codeine, oxycontin, morphine, ethylmorphine hydrochloride, diacetylmorphine, hydromorphone, dihydrocodeine, dihydromorphine and metformin, Particularly, prior to conjugating with the hydrophilic polymer, the non-naloxone opioid receptor antagonist is naltrexone, N-methylnaltrexone, nalmefene or nalbuphine.

In some embodiments, m is 1, 3, 4, 5, 6, 7, 8, 9, 10, or an integer between any two of the above values. Preferably, m is 2, i.e. there are two non-naloxone opioid receptor antagonists in the conjugate.

In another aspect, the present disclosure provides a conjugate represented by formula (II) or a pharmaceutically acceptable salt thereof:

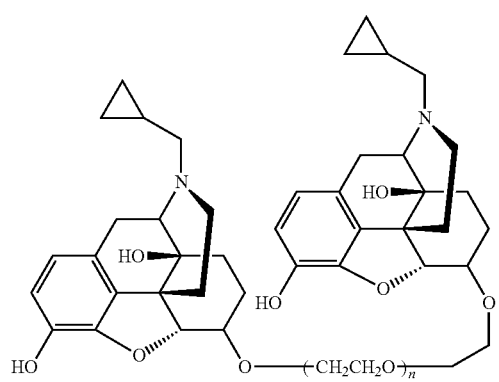

wherein, n is a natural number from 2 to 20.

In another aspect, the present disclosure provides a conjugate represented by formula (III) or a pharmaceutically acceptable salt thereof:

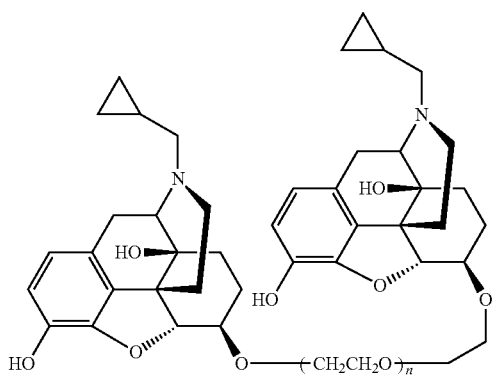

(III)

wherein, n is a natural number from 2 to 20.

In another aspect, the present disclosure provides a conjugate represented by formula (IV) or a pharmaceutically acceptable salt thereof:

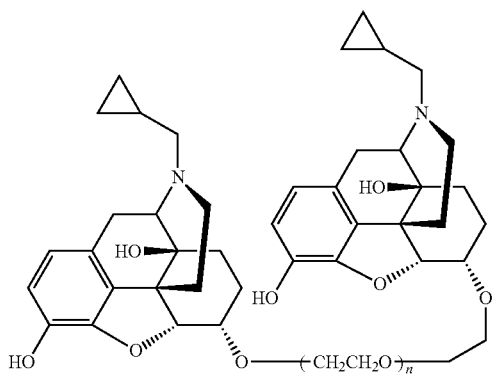

(IV)

wherein, n is a natural number from 2 to 20.

In some embodiments, n is 2, 3, 4, 5, 6, 7, 8, 9, 10, 11, 12, 13, 14, 15, 16, 17, 18, 19, 20 or an integer between any two of the above values.

In one embodiment, the hydrophilic polymer is a monodisperse polyethylene glycol having 8 —CH$_2$CH$_2$O— structural units, and wherein the non-naloxone opioid receptor antagonist prior to conjugation is two naltrexone molecules.

In one more aspect, the present disclosure provides a conjugate selected from the group consisting of PEG3-(6-α-naltrexol)2-ether, PEG4-(6-α-naltrexol)2-ether, PEG6-(6-α-naltrexol)2-ether, PEG8-(6-α-naltrexol)2-ether, PEG10-(6-α-naltrexol)2-ether, PEG4-(6-β-naltrexol)2-ether, PEG6-(6-β-naltrexol)2-ether, PEG8-(6-β-naltrexol)2-ether, mPEG6-(6-α-naltrexol)-ether, mPEG8-(6-α-naltrexol)-ether and mPEG6-(6-β-naltrexol)-ether.

In another aspect, the present disclosure provides a conjugate as represented by formula (V) or a pharmaceutically acceptable salt thereof:

$$W_1\text{—}P\text{—}W_2 \quad (V)$$

wherein P is a polyethylene glycol having 2 to 10 (for example, 2, 3, 4, 5, 6, 7, 8, 9, 10 or an integer between any two of the above values) —CH$_2$CH$_2$O— structural unit, and $W_1$ and $W_2$ are independently selected from activated forms or derivative forms of naltrexone, N-methylnaltrexone, nalmefene and nalbuphine.

In some embodiments, $W_1$ and $W_2$ each independently has the following structure:

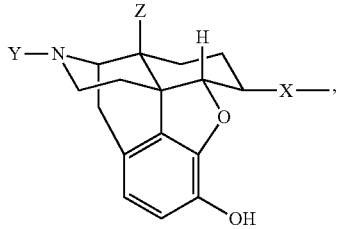

wherein
Y is

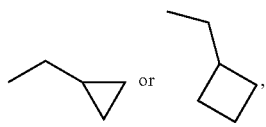

Z is —OH, and

X is amide group, amine group, carbamate group, thioether group, ether group, urea group or methylene group.

In some embodiments, the configurations of $W_1$ and $W_2$ are each independently, selected from α and β. For example, the configurations of $W_1$ and $W_2$ are (α, α), (β, β), (α, β), or a mixture thereof.

In other specific embodiments, each $W_1$ and $W_2$ independently is:

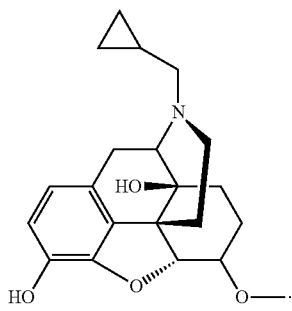

In other specific embodiments, each $W_1$ and $W_2$ independently is:

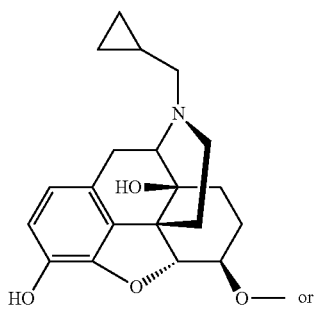

or

-continued

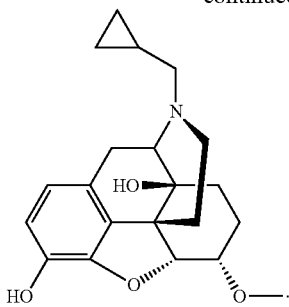

In another aspect, the present disclosure provides a pharmaceutical composition, the pharmaceutical composition comprises the conjugate of the present disclosure and optionally a pharmaceutically acceptable carrier.

In some embodiments, the pharmaceutical composition may be formulated to a tablet, injection, suppository, pill, soft and hard gelatin capsule, powders, solution, suspension or aerosol.

In one more aspect, the present disclosure provides a use of the conjugate or pharmaceutical composition according to the present disclosure in the manufacture of a medicine for the treatment of functional bowel disorders caused by opioid receptors, such as constipation.

In one more aspect, the present disclosure provides a use of the conjugate or pharmaceutical composition according to the present disclosure in the manufacture of a medicine for the treatment of pain in combination with an opioid.

In one more aspect, the present disclosure provides a use of the conjugate or pharmaceutical composition according to the present disclosure in the manufacture of a medicine for reducing opioid side effects.

In one more aspect, the present disclosure provides a use of the conjugate or pharmaceutical composition according to the present disclosure in the manufacture of a medicine for preventing the abuse of opioids.

In one more aspect, the present disclosure provides a kit, which comprises the conjugate or pharmaceutical composition according to the present disclosure and optionally an instruction for use.

In one aspect, the present disclosure provides a conjugate and/or pharmaceutical composition, which is used for the treatment of functional bowel disorders induced by opioid receptors, such as constipation.

In one more aspect, the present disclosure provides a conjugate and/or pharmaceutical composition, which is used for the treatment of pain in combination with an opioid.

In one more aspect, the present disclosure provides a conjugate and/or pharmaceutical composition, which is used for reducing opioid side effects.

In one more aspect, the present disclosure provides a conjugate and/or pharmaceutical composition, which is used for preventing the abuse of opioids In one more aspect, the present disclosure provides a method for treating functional bowel disorders induced by opioid receptors, such as constipation, comprising administering to an object in need thereof an effective amount of the conjugate and/or pharmaceutical composition according to the present disclosure.

In one more aspect, the present disclosure provides a method for treating pain in combination with an opioid, comprising administering to a subject in need thereof an effective amount of the conjugate and/or pharmaceutical composition according to the present disclosure.

In one more aspect, the present disclosure provides a method for reducing opioid side effects, comprising administering to an object in need thereof an effective amount of the conjugate and/or pharmaceutical composition according to the present disclosure.

The advantages of the present disclosure are at least that the modification of the water-soluble polymer polyethylene glycol can provide protections to naltrexone, improve drug absorption, change the distribution of the drug in vivo, reduce the ratio of passing through the blood-brain barrier, and avoid toxic and side effects.

BRIEF DESCRIPTION OF THE DRAWING

The above-described and other aspects of the present disclosure will be clearly explained according to the detailed description and drawings of the present disclosure. To exemplify the present disclosure, the embodiments in the drawings are preferred are present, however, it is understood that the present disclosure is not limited to the disclosed specific embodiments.

FIG. 1. A dose-response curve of Na1029 antagonizing the antidiarrheal effect of loperamide hydrochloride.

DETAILED DESCRIPTION

Definitions

The terms "activated form" or "derived form" (which are used interchangeably) as used herein refers to a compound in a particular position of which, a reactive group is introduced or a group is modified to a reactive functional group thereof to make the compound capable of coupling with a water soluble molecular.

The "opioid receptor antagonist" mentioned herein is a class of compounds having similar structure to that of opioids, without agonistic effect on opioid receptors themselves, but antagonizing opioid analgesics and removing opioid analgesics which bind with receptors or competitively bind with analgesics and eliminate side effects such as functional bowel disorders and respiratory depression induced by the use of some opioid analgesics.

The "polyethylene glycol" mentioned herein has the meaning commonly understood by those of ordinary skill in the art, including both polyethylene glycol (including bifurcation structures with different structures such as linear, branched, star) itself as well as derivatives with modified ends, unless otherwise explicitly stated. For example, the PEG is methoxypolyethylene glycol (mPEG). Herein, the terminal group of polyethylene glycol (PEG) is a hydroxyl group or other groups, unless otherwise specified. The other groups include, but are not limited to, alkoxy group, cycloalkoxy group, cycloalkyloxy group, alkenyl group, aryloxy group or aralkyloxy, group. These types of PEG molecule are known in the art and are routinely used in polypeptide modification. The PEG side chain can be linear, branched, bifurcated or consists of multiple arms, and different polyethylene glycols may have different polymeric chain lengths and polymeric structures. In a preferred embodiment of the present disclosure, the polyethylene glycol of the present disclosure is an oligo ethylene glycol, for example the repeating units are less than 20, 15, 10 and the like. More preferably, the polyethylene glycol of the present disclosure is monodispersed.

The "conjugate" mentioned herein refers to a product formed by a conjugation between a biologically active molecule (e.g., an opioid receptor antagonist) and a hydrophilic polymer molecule (e.g., polyethylene glycol) via covalent bond through direct linkage or by a linker.

The "pharmaceutically acceptable salt" mentioned herein may be hydrochloride, hydrobromide, sulfate, nitrate, phosphate, tartrate, fumarate, maleate, lactate, benzene sulfonate, pantothenate, ascorbate, etc., or a combination thereof. Preferably, the pharmaceutically, acceptable salt is a hydrochloride salt.

The "monodisperse" mentioned herein refers to that the polymer of the present disclosure (e.g., polyethylene glycol) are homogeneous, for example, the molar percentage of non-target products is less than 10%, 8%, 5%, 3%, 2%, 1%, 0.5%, 0.1%, 0.01% or 0.001%.

Terms used herein such as "including", "containing" and "comprising" are not intended to limit. In addition, "or" means "and/or" unless otherwise stated.

In addition, it should be noted that, as used in the specification, the singular form includes the plural form of the subject matter to which it refers unless it is clearly and explicitly limited to one object. And if a specific value is mentioned, it at least includes the value unless the article otherwise clearly indicates.

When a numerical value indicates approximate value, it should be interpreted as that a particular value forms another embodiment. As what is used, "about X" (where X is a numerical value) refers to ±10% (inclusive) of the value listed. If exists, all ranges are included and can be combined.

The term "pharmaceutical composition" used herein represents a combination of at least one medicine and optionally a pharmaceutically acceptable carrier or excipient combining together to achieve a particular purpose. In certain embodiments, the pharmaceutical composition includes combinations that are separated in time and/or space, as long as they are capable of working together to achieve the purposes of the present disclosure. For example, the components of the pharmaceutical composition (for example, the conjugate according to the present disclosure) may be administered to the object as a whole or separately. When the components of the pharmaceutical composition are separately administered to an object, the components may be administered to the object simultaneously or sequentially. Preferably, said pharmaceutically acceptable carrier is water, buffered aqueous solution, isotonic saline solution such as PBS (phosphate buffer), glucose, mannitol, dextrose, lactose, starch, magnesium stearate, fiber, magnesium carbonate, 0.3% glycerol, hyaluronic acid, ethanol, or polyalkylene glycol such as polypropylene glycol, triglyceride and the like. The type of the pharmaceutically acceptable carrier used depends particularly on the administration manner of the composition according to the present disclosure, for example, oral, nasal, intradermal, subcutaneous, intramuscular or intravenous administration. The composition according to the present disclosure may contain, as an additive, a lubricant, a preservative, a stabilizer, a wetting agent, an emulsifier, a salt which affects the osmotic pressure, a buffer, a coloring matter, a flavoring substance, and/or an aromatic substance.

The pharmaceutical compositions according to the present disclosure may be administered by any suitable way, for example, orally, nasally, intradermally, subcutaneously, intramuscularly or intravenously.

"Administering" means providing a substance to an object in a pharmacologically available manner.

The "pharmaceutically effective amount" and "effective amount" used herein refers to a dose which is sufficient to show its benefit to the object to which it is administered. The actual administered amount, as well as the rate and time course of administration, depend on the condition and severity of the object being treated. The prescription for treatment (e.g., the determination of the dose) is ultimately the responsibility of the general practitioner and other physicians and relied on them to make decisions, usually the disease being treated, the condition of the individual patient, the site of delivery, the method of administration, and the other factors known to the doctors are considered.

The term "object" used herein means animals, including warm-blooded mammals, such as humans and primates; birds; domesticated or farm animals, such as cats, dogs, sheep, goats, cows, horses; and pigs; laboratory animals such as mice, rats and guinea pigs; fish; reptiles; zoo animals and wild animals.

Unless otherwise defined, all technical and scientific terms used herein have the same meaning as understood by those having ordinary skill in the art.

Unless otherwise defined, any component, element, attribute or step disclosed about an embodiment of the method and product may be applied to any of the other methods and products disclosed herein.

Each of the patents, patent applications and cited publications in the present disclosure or the descriptions in the present disclosure are hereby entirely incorporated by reference.

The invention is further defined in the following embodiments. It should be understood that the embodiments are only examples for illustration purpose rather than intending to limit the scope of the present invention. From the discussion and the examples above, those having ordinary skill in the art can determine the essential characteristics of the present invention and make changes and modifications to the present invention in various aspects to adapt it to various usages and conditions without departing from its essential and scope.

EXAMPLES

Example 1: Preparation of Polyethylene Glycol Mesylate

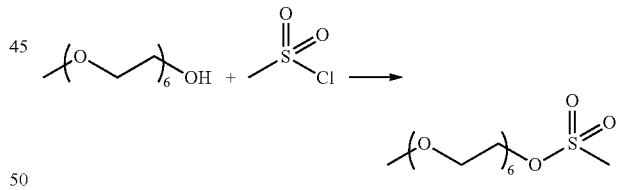

50 ml of dichloromethane, 7.18 ml of triethylamine, 206 mg of p-dimethylaminopyridine and 10.0 g of $CH_3$—$(OCH_2CH_2)_6$—OH (abbreviated as mPEG6-OH) (Jiaxing Biomatrik, M006110503) were successively added to a reaction flask. A solution of 3.28 ml of methanesulfonyl chloride in 50 ml of dichloromethane was added dropwise with stirring at 0° C. After the completion of the dropwise addition, the reaction was stirred at room temperature overnight. The reaction solution was transferred to a separatory funnel and washed with dilute hydrochloric acid and brine successively. The organic layer was separated, dried with 30 g of anhydrous sodium sulfate. After the desiccant was filtered out, the organic layer was concentrated by rotary evaporation to obtain 13.6 g of crude product. The crude product was purified by chromatography to obtain 13.0 g of mPEG6-OMs ($CH_3$—$(OCH_2CH_2)_6$—$OSO_2CH_3$). 1H-NMR (400 MHz, CDCl3), δ ppm 4.35-4.41 (2H, m), 3.74-3.80 (2H, m), 3.60-3.70 (18H, m), 3.52-3.58 (2H, m), 3.38 (3H, s), 3.08 (3H, s).

Using a similar procedure, with different polyethylene glycols as starting materials, a variety of polyethylene glycol mesylate as listed in the table below could be prepared.

TABLE 1

Polyethylene glycol mesylate used in the present disclosure

| Abbreviation | Molecular Structure |
|---|---|
| PEG3-(OMs)2 | $CH_3SO_2$—$(OCH_2CH_2)_3$—$OSO_2CH_3$ |
| PEG4-(OMs)2 | $CH_3SO_2$—$(OCH_2CH_2)_4$—$OSO_2CH_3$ |
| PEG6-(OMs)2 | $CH_3SO_2$—$(OCH_2CH_2)_6$—$OSO_2CH_3$ |
| PEG8-(OMs)2 | $CH_3SO_2$—$(OCH_2CH_2)_8$—$OSO_2CH_3$ |
| PEG10-(OMs)2 | $CH_3SO_2$—$(OCH_2CH_2)_{10}$—$OSO_2CH_3$ |
| mPEG6-OMs | $CH_3$—$(OCH_2CH_2)_6$—$OSO_2CH_3$ |
| mPEG8-OMs | $CH_3$—$(OCH_2CH_2)_8$—$OSO_2CH_3$ |

The specific preparation process is as follows:

PEG3-(OMs)2: 50 ml of dichloromethane, 17.0 ml of triethylamine, 244 mg of p-dimethyaminopyridine and 6.00 g of H—$(OCH_2CH_2)_3$—OH (abbreviated as H-PEG3-OH) (Sinopharm Reagent, 20130125) were successively added to a reaction flask. A solution of 7.8 ml of methanesulfonyl chloride in 20 ml of dichloromethane was added dropwise with stirring at 5 to 10° C. After the completion of the dropwise addition, the reaction was stirred at room temperature overnight. The reaction solution was transferred to a separatory funnel and washed with dilute hydrochloric acid and brine successively. The organic layer was separated, dried with 30 g of anhydrous sodium sulfate. After the desiccant was filtered out, the organic layer was concentrated by rotary evaporation to obtain 12.6 g of crude product. The crude product was purified by chromatography to obtain 11.2 g of pure product. 1H-NMR (400 MHz, CDCl3), δ ppm 4.34-4.41 (4H, m), 3.74-3.80 (4H, m), 3.68 (4H, s), 3.07 (6H, s).

PEG4-(OMs)2: 50 ml of dichloromethane, 17.0 ml of triethylamine, 244 mg of p-dimethylaminopyridine and 7.76 g of H—$(OCH_2CH_2)_4$—OH (abbreviated as H-PEG4-OH) (Aladdin Reagent, J1218031) were successively added to a reaction flask. A solution of 7.8 ml of methanesulfonyl chloride in 50 ml of dichloromethane was added dropwise with stirring at 0° C. After the completion of the dropwise addition, the reaction was stirred at room temperature overnight. The reaction solution was transferred to a separatory funnel and washed with dilute hydrochloric acid and brine successively. The organic layer was separated, dried with 30 g of anhydrous sodium sulfate. After the desiccant was filtered out, the organic layer was concentrated by rotary evaporation to obtain 14.7 g of crude product. The crude product was purified by chromatography to obtain 13.90 g of pure product. 1H-NMR (400 MHz, CDCl3), δ ppm 4.34-4.41 (4H, m), 3.73-3.81 (4H, m), 3.60-3.71 (8H, m), 3.07 (6H, s).

PEG6-(OMs)2: 50 ml of dichloromethane, 10.625 ml of triethylamine, 152.5 mg of p-dimethylaminopyridine and 7.05 g of H—$(OCH_2CH_2)_6$—OH (abbreviated as H-PEG6-OH) (Jiaxing Biomatrik, DH06141230) were successively added to a reaction flask. A solution of 4.875 ml of methanesulfonyl chloride in 40 ml of dichloromethane was added dropwise with stirring at 5-8° C. After the completion of the dropwise addition, the reaction was stirred at room temperature overnight. The reaction solution was transferred to a separatory funnel and washed with dilute hydrochloric acid and brine successively. The organic layer was separated, dried with 30 g of anhydrous sodium sulfate. After the desiccant was filtered out, the organic layer was concentrated by rotary evaporation to obtain 12.5 g of crude product. The crude product was purified by chromatography to obtain 10.5 g of pure product. 1H-NMR (400 MHz, CDCl3), δ ppm 4.34-4.41 (4H, m), 3.73-3.81 (4H, m), 3.60-3.71 (16H, m), 3.08 (6H, s).

PEG8-(OMs)2: 50 ml of dichloromethane, 5.74 ml of triethylamine, 83 mg of p-dimethylaminopyridine and 5.0 g of H—$(OCH_2CH_2)_8$—OH (abbreviated as H-PEG8-OH) (Jiaxing Biomatrik, DH08150114) were successively added to a reaction flask. A solution of 2.64 ml of methanesulfonyl chloride in 50 ml of dichloromethane was added dropwise with stirring at 0° C. After the completion of the dropwise addition, the reaction was stirred at room temperature overnight. The reaction solution was transferred to a separatory funnel and washed with dilute hydrochloric acid and brine successively. The organic layer was separated, dried with 30 g of anhydrous sodium sulfate. After the desiccant was filtered out, the organic layer was concentrated by rotary evaporation to obtain 8.17 g of crude product. The crude product was purified by chromatography to obtain 6.7 g of pure product. 1H-NMR (400 MHz, CDCl3), δ ppm, 4.34-4.41 (4H, m), 3.73-3.81 (4H, m), 3.60-3.71 (24H, m), 3.08 (6H, s).

PEG10-(OMs)2: 50 ml of dichloromethane, 4.63 ml of triethylamine, 66.5 mg of p-dimethylaminopyridine and 5.0 g of H—$(OCH_2CH_2)_{10}$—OH (abbreviated as H-PEG10-OH) (Jiaxing Biomatrik, DH10140509) were successively added to a reaction flask. A solution of 2.13 ml of methanesulfonyl chloride in 50 ml of dichloromethane was added dropwise with stirring at 0° C. After the completion of the dropwise addition, the reaction was stirred at room temperature overnight. The reaction solution was transferred to a separatory funnel and washed with dilute hydrochloric acid and brine successively. The organic layer was separated, dried with 30 g of anhydrous sodium sulfate. After the desiccant was filtered out, the organic layer was concentrated by rotary evaporation to obtain 8.0 g of crude product. The crude product was purified by chromatography to obtain 5.5 g of pure product. 1H-NMR (400 MHz, CDCl3), δ ppm, 4.34-4.41 (4H, m), 3.73-3.81 (4H, m), 3.60-3.71 (32H, m), 3.08 (6H, s).

mPEG8-OMs: 50 ml of dichloromethane, 2.763 ml of triethylamine, 80 mg of p-dimethylaminopyridine and 5.0 g of $CH_3$—$(OCH_2CH_2)_8$—OH (abbreviated as mPEG8-OH) (Jiaxing Biomatrik, M008131031) were successively added to a reaction flask. A solution of 1.27 ml of methanesulfonyl chloride in 50 ml of dichloromethane was added dropwise with stirring at 0° C. After the completion of the dropwise addition, the reaction was stirred at room temperature overnight. The reaction solution was transferred to a separatory funnel and washed with dilute hydrochloric acid and brine successively. The organic layer was separated, dried with 30 g of anhydrous sodium sulfate. After the desiccant was filtered out, the organic layer was concentrated by rotary evaporation to obtain 7.0 g of crude product. The crude product was purified by chromatography to obtain 5.44 g of purified product. 1H-NMR (400 MHz, CDCl3), δ ppm 4.35-4.41 (2H, m), 3.74-3.80 (2H, m), 3.60-3.70 (26H, m), 3.52-3.58 (2H, m), 3.38 (3H, s), 3.08 (3H, s).

Example 2: Preparation of 3-MOM-Naltrexone and 3-MOM-Naloxone

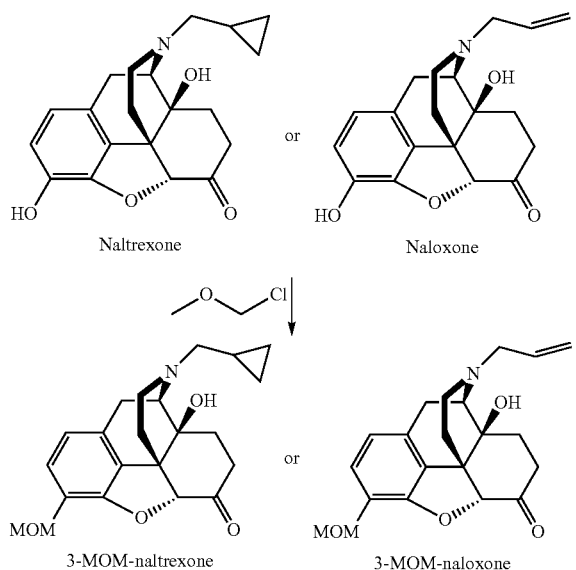

200 ml of dichloromethane, 41.7 g of diisopropylethylamine and 19.83 g of naltrexone hydrochloride (Jinan Haohua Industrial Co., Ltd., FR00007) were successively added to a reaction flask. A solution of 17.7 g of chlorotnethyl methyl ether in 200 ml of dichlorornethane was added dropwise with stirring at 0° C. After the dropwise addition was completed, the reaction was stirred overnight. The reaction solution was transferred to a separatory funnel and washed with an alkali solution (400 ml of water +40 g of anhydrous sodium carbonate +10.0 g of sodium hydroxide +30 g of sodium chloride, well mixed). The organic layer was separated, dried with 30 g of anhydrous sodium sulfate. After the desiccant was filtered out, the organic layer was concentrated by rotary evaporation to obtain 21.3 g of product 3-MOM-naltrexone. 1H-NMR. (400 MHz, CDCl3), δ ppm 6.85-6.92 (1H, d, J=8.0 Hz), 6.58-6.65 (1H, d, J=8.4 Hz), 5.20-5.30 (2H, m), 4.68 (1H, s), 3.52 (3H, s), 3.15-3.22 (1H, d, J=6.0 Hz), 2.97-3.12 (2H, m), 2.66-2.75 (1H, m), 2.54-2.64 (1H, m), 2.37-2.50 (3H, m), 2.26-2.35 (1H, m), 2.10-2.20 (1H, m), 1.83-1.93 (1H, m), 1.54-1.71 (2H, m), 0.81-0.92 (1H, m), 0.52-0.62 (2H, m), 0.11-0.19 (2H, m). LC/MS (ESI) m/z 386.5 [M+H]+.

50 ml of dichloromethane, 13.51 g of diisopropylethylamine and 5.00 g of naloxone hydrochloride (Jinan Haohua Industrial Co., Ltd., GR00037) were successively added to a reaction flask. A solution of 5.55 g of chloromethyl methyl ether in 50 nil of dichloromethane was added dropwise with stirring at 0° C. After the dropwise addition was completed, the reaction was stirred overnight. The reaction solution was transferred to a separatory funnel and washed with an alkali solution (100 ml of water +10 g of anhydrous sodium carbonate +3.0 g of sodium hydroxide +7 g of sodium chloride, well mixed). The organic layer was separated, dried with 10 g of anhydrous sodium sulfate. After the desiccant was filtered out, the organic layer was concentrated by rotary evaporation to obtain 5.14 g of product 3-MOM-naloxone. 1H-NMR (400 MHz, CDCl3), δ ppm 6.86-6.92 (1H, d, J=8.4 Hz), 6.59-6.66 (1H, d, J=8.4 Hz), 5.76-5.90 (1H, m), 5.15-5.30 (4H, m), 5.02 (1H, s), 4.67 (1H, s), 3.52 (3H, s), 3.14-3.19 (2H, m), 3.06-3.14 (1H, d, J=18.4 Hz), 2.96-3.07 (2H, m), 2.53-2.64 (2H, m), 2.34-2.44 (1H, m), 2.25-2.33 (1H, m), 2.10-2.20 (1H, m), 1.82-1.92 (1H, m), 1.54-1.68 (2H, m). LC/MS (ESI) m/z 372.5[M+H]+.

Example 3: Preparation of 3-MOM-6-α-Naltrexol and 3-MOM-6-α-Naloxol

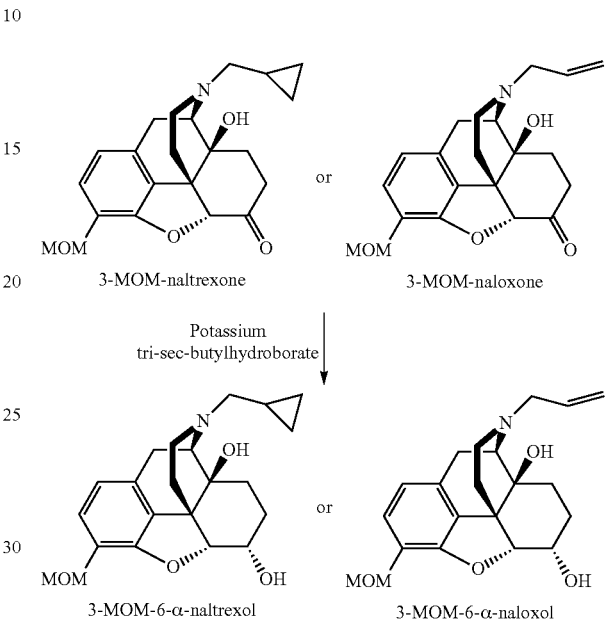

Under the protection of argon, 100 ml of tetrahydrofuran and 16.8 g of 3-MOM-naltrexone were added to a reaction flask. 45 ml of a solution of potassium tri-sec-butylborohydride in tetrahydrofuran was added under stirring at 10° C. The reaction was monitored using thin-layer chromatography (TLC). After the reaction was completed, the pH was adjusted to 2 to 4 with dilute hydrochloric acid. The reaction solution was transferred to a separatory funnel and extracted four times with dichloromethane (150, 100, 100, 100 ml). The organic layers were separated, and 10.0 g of sodium hydroxide in 150 ml of aqueous solution was added to the aqueous layer, and the mixture was mixed well and extracted three times with dichloromethane (100 ml×3). The organic layers were combined, dried with 20 g of anhydrous sodium sulfate. After the desiccant was filtered out, the organic layer was concentrated by rotary evaporation to obtain 16.5 g of product 3-MOM-6-α-naltrexol. 1H-NMR (400 MHz, CDCl3), δ ppm 6.78-6.88 (1H, d, J=8.0 Hz), 6.54-6.64 (1H, d, J=8.4 Hz), 5.53-5.62 (1H, d, J=6.4 Hz), 5.29 (1H, s), 5.05 (1H, s), 4.96-5.02 (1H, d, J=6.4 Hz), 4.58-4.68 (1H, d, J=5.2 Hz), 4.12-4.24 (1H, m), 3.48 (3H, s), 2.98-3.12 (3H, m), 2.55-2.70 (2H, m), 2.33-2.42 (2H, d, J=6.8 Hz), 2.15-2.31 (2H, m) 1.48-1.60 (3H, m), 1.28-1.42 (1H, 0.78-0.91 (1H, m), 0.49-0.60 (2H, m), 0.09-0.18 (2H, m). LC/MS (ESI) m/z 388.5 [M+H]+.

Under the protection of argon, 20 ml of tetrahydrofuran and 3.48 g of 3-MOM-naloxone were added to a reaction flask. 13 ml of a solution of potassium tri-sec-butylborohydride in tetrahydrofuran was added under stirring at −15° C. The reaction was monitored using thin-layer chromatography (TLC). After the reaction was completed, the pH was adjusted to 3 to 5 with dilute hydrochloric acid. The reaction solution was transferred to a separatory funnel and extracted four times with dichloromethane (50 ml×4). The organic layers were separated, and 1.0 g of sodium hydroxide in 50 ml of aqueous solution was added to the aqueous layer, and the mixture was mixed well and extracted three times with dichloromethane (50 ml×3). The organic layers were combined, dried with 10 g of anhydrous sodium sulfate. After the desiccant was filtered out, the organic layer was concentrated by rotary evaporation to obtain 2.97 g of product 3-MOM-6-α-naloxol. 1H-NMR (400 MHz, CDCl3), ppm 6.80-6.86 (1H, d, J=8.4 Hz), 6.57-6.63 (1H, d, J=8.4 Hz), 5.73-5.87 (1H, m), 5.53-6.58 (1H, d, J=6.4 Hz), 5.12-5.24 (2H, m), 4.96-5.02 (1H, d, J=6.4 Hz), 4.88 (1H, s), 4.59-4.64 (1H, d, J=5.2 Hz), 4.13-4.21 (1H, m), 3.48 (3H, s), 3.02-3.14 (4H, m), 2.87-2.93 (1H, d, J=6.4 Hz), 2.48-2.66 (2H, m), 2.19-2.25 (2H, d, J=7.6 Hz), 1.82-1.95 (1H, m), 1.44-1.60 (3H, m), 1.27-1.39 (1H, m). LC/MS (ESI) m/z 374.5 [M+H]+.

Example 4: Preparation of 3-MOM-6-β-naltrexol and 3-MOM-6-β-naloxol

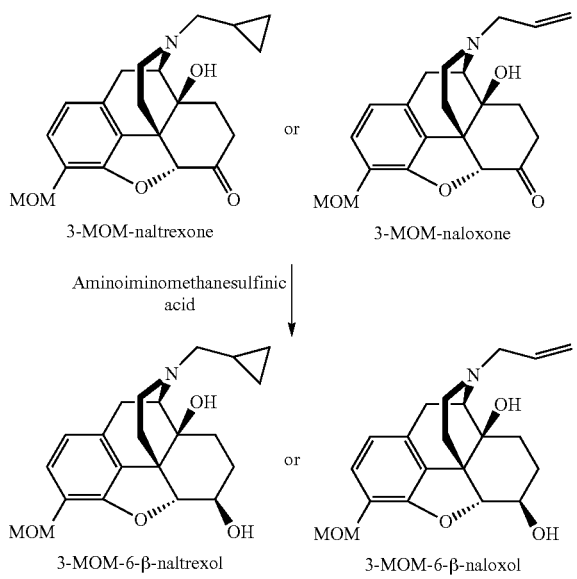

Under the protection of argon, 30 ml of ethanol, 1.64 g of an alkaline solution of 3-MOM-naloxone and aminoiminomethanesulfinic acid (1.74 g of aminoiminomethanesulfinic acid +0.85 g of sodium hydroxide 30 ml of water) were added to a reaction flask. Reaction was carried out at 80° C. with stirring and the reaction was monitored using TLC. After the reaction was completed, the heating was stopped. 120 ml of brine (10%) was added to the mixture, and the mixture was mixed well and then transferred to a separatory funnel and extracted three times with dichloromethane (50, 25, 25 nil). The organic layers were combined and washed with 10% brine. The organic layers were combined, dried with 10 g of anhydrous sodium sulfate. After the desiccant was filtered out, the organic layer was concentrated by rotary evaporation to obtain 1.29 g of product 3-MOM-6-β-naloxol. 1H-NMR (400 MHz, CDCl3), δ ppm 6.87-6.93 (1H, d, J=8.4 Hz), 6.58-6.64 (1H, d, J=8.4 Hz), 5.73-5.87 (1H, m), 5.10-5.26 (4H, m), 4.96-5.02 (1H, d, J=6.4 Hz), 4.46-4.52 (1H, d, J=5.6 Hz), 3.54-3.64 (1H, m), 3.50 (3H, s), 3.03-3.16 (3H, m), 2.90-2.96 (1H, d, J=5.6 Hz), 2.50-2.66 (2H, m), 2.10-2.28 (2H, m), 1.86-2.02 (1H, m), 1.54-1.68 m), 1.46-1.54 (1H, m), 1.30-1.40 (1H, m). LC/MS (ESI) m/z 374.5 [M+H]+.

Under the protection of argon, 80 ml of ethanol, 4.51 g of an alkali solution of 3-MOM-naltrexone and aminoiminomethanesulfinic acid (4.33 g of aminoiminomethanesulfinic acid +2.06 g of sodium hydroxide +80 ml of water) were added to a reaction flask. Reaction was carried out at 80° C. with stirring and the reaction was monitored using TLC. After the reaction was completed, the heating was stopped, 300 ml of brine (10%) was added, and the mixture was well mixed and transferred to a separatory funnel and extracted three times with dichloromethane (100, 50, 50 ml). The organic layers were combined and washed with 10% brine. The organic layers were combined, dried with 20 g of anhydrous sodium sulfate. After the desiccant was filtered out, the organic layer was concentrated by rotary evaporation to obtain 4.10 g of product 3-MOM-6-β-naltrexol. 1H-NMR (400 MHz, CDCl3), δ ppm 6.87-6.93 (1H, d, J=8.4 Hz), 6.57-6.63 (1H, d, 0.1=8.0 Hz), 5.15-5.26 (2H, m), 5.29 (1H, s), 4.46-4.53 (1H, d, J=5.6 Hz), 3.54-3.64 (1H, m), 3.50 (3H, s), 3.00-3.14 (2H, m), 2.86-2.98 (1H, m), 2.55-2.70 (2H, m), 2.33-2.40 (2H, d, J=6.4 Hz), 2.19-2.30 (1H, m), 2.09-2.20 (1H, m), 1.88-2.04 (1H, m), 1.55-1.70 (2H, m), 1.47-1.54 (1H, m), 1.32-1.43 (1H, m), 0.78-0.91 (1H, m), 0.48-0.60 (2H, m), 0.05-0.18 (2H, m). LC/MS (ESI) m/z 388.6 [M+H]+.

Example 5: Preparation of PEGylated Naltrexol and Naloxol, and Hydrochlorides Thereof

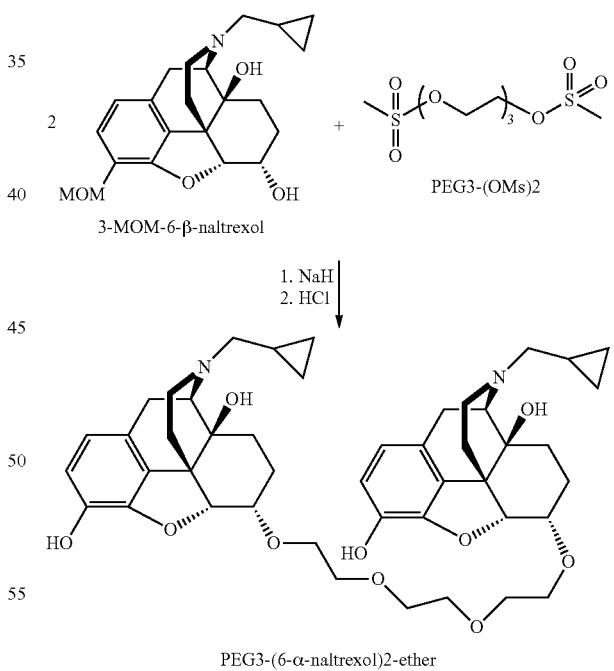

PEG3-(6-α-naltrexol)2-ether

Under the protection of argon, 1.00 g of sodium hydride and 20 ml of dimethylformamide were added to a reaction flask and stirred to be a suspension. Then, 2.02 g of 3-MOM-6-α-naltrexol in 12 ml of tetrahydrofuran and 661 mg of PEG3-(OMs)2 in 12 ml of tetrahydrofuran were successively added. The temperature was raised to 60° C., reaction was carried out with stirring and monitored using TLC. After the reaction was completed, excess sodium hydride was quenched with water. The reaction solution was concentrated by rotary evaporation, the resulting residue was extracted with dichloromethane and water system, and the organic layer was separated. The organic layer was washed five times with a 5% aqueous sodium carbonate solution, separated and dried with anhydrous sodium sulfate. After the desiccant was removed, the organic layer was concentrated by rotary evaporation to obtain 2.45 g of residue. Then said residue was treated with 15 ml of hydrochloric acid (4.0 M) and stirred at room temperature overnight. After the reaction was completed, the pH of the reaction solution was adjusted to 3 to 5 with 4 M aqueous ammonia. Finally, chromatography purification was carried out to obtain 0.55 g of PEG3-(6-α-naltrexol)2-ether (abbreviated as Nal053) product.

The above-mentioned product was dissolved in 20 ml of ethanol, then 2.5 ml of hydrogen chloride ethanol solution (1.0 M) was added. The mixture was mixed well and then concentrated by rotary evaporation to obtain 0.65 g of residue. Said residue was dissolved in 20 ml of water and freeze-dried to obtain 0.45 g of almost white powdery solid, i.e. dihydrochloride salt of Nal053. 1H-NMR (400 MHz, D2O), δ ppm 6.72-6.77 (2H, d, J=8.4 Hz), 6.62-6.68 (2H, d, J=8.4 Hz), 4.81-4.86 (2H, d, J=4.8 Hz), 3.90-4.00 (4H, m), 3.66-3.74 (2H, m), 3.59-3.66 (2H, m), 3.46-3.59 (4H, m), 3.45 (4H, s), 3.25-3.34 (2H, d, J=19.6 Hz), 3.17-3.25 (2H, m), 3.03-3.14 (4H, m), 2.87-2.97 (2H, m), 2.73-2.87 (2H, m), 2.35-2.47 (2H, m), 1.68-1.79 (2H, m), 1.47-1.69 (6H, m), 1.16-1.30 (2H, m), 0.92-1.04 (2H, m), 0.67-0.77 (2H, m), 0.57-0.67 (2H, m), 0.28-0.43 (4H, m). LC/MS (ESI) m/z 802.1 [M+H]+ and 401.8 [M+2H]++.

Using a similar procedure, with different polyethylene glycols as starting materials (as shown in Table 3), a variety of PEGylated naltrexol and naloxol, and hydrochlorides thereof as listed in table 2 below could be prepared.

TABLE 2

Conjugates of the Present Disclosure

| Abbreviation | Molecular Structure | Chemical Formula | Hydrochloride Form |
|---|---|---|---|
| Nal053 | PEG3-(6-α-naltrexol)2-ether | $C_{46}H_{60}N_2O_{10}$ | $C_{46}H_{60}N_2O_{10} \cdot 2HCl$ |
| Nal021 | PEG4-(6-α-naltrexol)2-ether | $C_{48}H_{64}N_2O_{11}$ | $C_{48}H_{64}N_2O_{11} \cdot 2HCl$ |
| Nal025 | PEG6-(6-α-naltrexol)2-ether | $C_{52}H_{72}N_2O_{13}$ | $C_{52}H_{72}N_2O_{13} \cdot 2HCl$ |
| Nal029 | PEG8-(6-α-naltrexol)2-ether | $C_{56}H_{80}N_2O_{15}$ | $C_{56}H_{80}N_2O_{15} \cdot 2HCl$ |
| Nal033 | PEG10-(6-α-naltrexol)2-ether | $C_{60}H_{88}N_2O_{17}$ | $C_{60}H_{88}N_2O_{17} \cdot 2HCl$ |
| Nal022 | PEG4-(6-β-naltrexol)2-ether | $C_{48}H_{64}N_2O_{11}$ | $C_{48}H_{64}N_2O_{11} \cdot 2HCl$ |
| Nal026 | PEG6-(6-β-naltrexol)2-ether | $C_{52}H_{72}N_2O_{13}$ | $C_{52}H_{72}N_2O_{13} \cdot 2HCl$ |
| Nal030 | PEG8-(6-β-naltrexol)2-ether | $C_{56}H_{80}N_2O_{15}$ | $C_{56}H_{80}N_2O_{15} \cdot 2HCl$ |
| Nal037 | mPEG6-(6-α-naltrexol)-ether | $C_{33}H_{51}NO_{10}$ | $C_{33}H_{51}NO_{10} \cdot HCl$ |
| Nal041 | mPEG8-(6-α-naltrexol)-ether | $C_{37}H_{59}NO_{12}$ | $C_{37}H_{59}NO_{12} \cdot HCl$ |
| Nal038 | mPEG6-(6-β-naltrexol)-ether | $C_{33}H_{51}NO_{10}$ | $C_{33}H_{51}NO_{10} \cdot HCl$ |
| Nal045 | mPEG6-(6-α-naloxol)-ether | $C_{32}H_{49}NO_{10}$ | $C_{32}H_{49}NO_{10} \cdot HCl$ |
| Nal049 | mPEG8-(6-α-naloxol)-ether | $C_{36}H_{57}NO_{12}$ | $C_{36}H_{57}NO_{12} \cdot HCl$ |
| Nal046 | mPEG6-(6-β-naloxol)-ether | $C_{32}H_{49}NO_{10}$ | $C_{32}H_{49}NO_{10} \cdot HCl$ |

TABLE 3

Raw Materials for Preparation of the Conjugate of the Present Disclosure

| | Raw Material 1 | | | |
|---|---|---|---|---|
| Raw Material 2 | 3-MOM-6-α-naltrexol | 3-MOM-6-β-naltrexol | 3-MOM-6-α-naloxol | 3-MOM-6-β-naloxol |
| PEG3-(OMs)2 | Nal053 | | | |
| PEG4-(OMs)2 | Nal021 | Nal022 | | |
| PEG6-(OMs)2 | Nal025 | Nal026 | | |
| PEG8-(OMs)2 | Nal029 | Nal030 | | |
| PEG10-(OMs)2 | Nal033 | | | |
| mPEG6-OMs | Nal037 | Nal038 | Nal045 | Nal046 |
| mPEG8-OMs | Nal041 | | Nal049 | |

Nal021: Under the protection of argon, 1.10 g of sodium hydride and 20 ml of dimethylformamide were added to a reaction flask and stirred to be a suspension. Then, 3.0 g of 3-MOM-6-α-naltrexol in 12 ml of tetrahydrofuran and 1.15 g of PEG4-(OMs)2 in 12 ml of tetrahydrofuran were subsequently added. The temperature was raised to 60° C., reaction was carried out with stirring and monitored using TLC. After the reaction was completed, excess sodium hydride was quenched with water. The reaction solution was concentrated by rotary evaporation, the resulting residue was extracted with dichloromethane and water system, and the organic layer was separated. The organic layer was washed five times with a 5% aqueous sodium carbonate solution, separated and dried with anhydrous sodium sulfate. After the desiccant was removed, the organic layer was concentrated by rotary evaporation to obtain a residue. Then said residue was treated with 15 ml of hydrochloric acid (4.0 M) and stirred at room temperature overnight. After the reaction was completed, the pH of the reaction solution was adjusted to 3 to 5 with 4 M aqueous ammonia. Finally, chromatography purification was carried out to obtain product PEG4-(6-α-naltrexol)2-ether. The above-mentioned product was dissolved in 20 ml of ethanol, then 3.0 ml of hydrogen chloride ethanol solution (1.0 M) was added, and the mixture was well mixed and then concentrated by rotary evaporation to obtain 1.43 g of residue. The resulting residue was dissolved in 20 ml of water and freeze-dried to obtain 0.97 g of almost white powdery solid, i.e. dihydrochloride salt of Nal021. 1H-NMR (400 MHz, D2O), δ ppm 6.72-6.77 (2H, d, J=8.0 Hz), 6.62-6.68 (2H, d, J=8.0 Hz), 4.81-4.86 (2H, d, J=4.8 Hz), 3.90-4.00 (4H, m), 3.66-3.74 (2H, m), 3.59-3.66 (2H, m), 3.45-3.59 (12H, m), 3.24-3.34 (2H, d, J=19.6 Hz), 3.16-3.24 (2H, m), 3.03-3.14 (4H, m), 2.86-2.97 (2H, m), 2.72-2.84 (2H, m), 2.35-2.47 (2H, m), 1.68-1.79 (2H, m), 1.47-1.68 (6H, m), 1.16-1.30 (2H, m), 0.91-1.04 (2H, m), 0.67-0.77 (2H, m), 0.57- 0.67 (2H, m), 0.28-0.43 (4H, m). LC/MS (ESI) m/z 846.0 [M+H]+ and 423.8 [M+2H]++.

Nal025: Under the protection of argon, 0.73 g of sodium hydride and 20 ml of dimethylformamide were added to a reaction flask and stirred to be a suspension. Then, 2.92 g of 3-MOM-6-α-naltrexol in 12 ml of tetrahydrofuran and 1.38 g of PEG6-(OMs)2 in 12 ml of tetrahydrofuran were subsequently added. The temperature was raised to 60° C., reaction was carried out with stirring and monitored using TLC. After the reaction was completed, excess sodium hydride was quenched with water. The reaction solution was concentrated by rotary evaporation, the resulting residue was extracted with dichloromethane and water system, and the organic layer was separated. The organic layer was washed five times with a 5% aqueous sodium carbonate solution, separated and dried with anhydrous sodium sulfate. After the desiccant was removed, the organic layer was concentrated by rotary evaporation to obtain 4.18 g of residue. Then said residue was treated with 15 ml of hydrochloric acid (4.0 M) and stirred at room temperature overnight. After the reaction was completed, the pH of the reaction solution was adjusted to 3 to 5 with 4 M aqueous ammonia. Finally, chromatography purification was carried out to obtain product PEG6-(6-α-naltrexol)2-ether. The above-mentioned product was dissolved in 20 ml of ethanol, then 3.0 ml of hydrogen chloride—ethanol solution (1.0 M) was added, and the mixture was well mixed and then concentrated by rotary evaporation to obtain 1.1 g of residue. The resulting residue was dissolved in 20 ml of water and freeze-dried to obtain 0.71 g of almost white powdery solid, i.e. dihydrochloride salt of Na1025. 1H-NMR (400 MHz, D2O), δ ppm 6.72-6.77 (2H, d, J=8.0 Hz), 6.62-6.68 (2H, d, J=8.0 Hz), 4.81-4.86 (2H, d, J=4.8 Hz), 3.90-4.00 (4H, m), 3.66-3.74 (2H, m), 3.59-3.66 (2H, m), 3.45-3.59 (20H, m), 3.24-3.34 (2H, d, 20.0 Hz)), 3.16-3.24 (2H, m), 3.03-3.14 (4H, m), 2.86-2.97 (2H, m), 2.72-2.84 (2H, m), 2.35-2.47 (2H, m), 1.68-1.79 (2H, m), 1.47-1.68 (6H, m), 1.16-1.30 (2H, m), 0.91-1.04 (2H, m), 0.67-0.77 (2H, m), 0.57-0.67 (2H, m), 0.28-0.43 (4H, m), LC/MS (ESI) m/z 934.1 [M+H]+ and 467.8 [M+2H]++.

Na1029: Under the protection of argon, 0.92 g of sodium hydride and 20 ml of dimethylformamide were added to a reaction flask and stirred to be a suspension. Then, 2.99 g of 3-MOM-6-α-naltrexol in 12 ml of tetrahydrofuran and 1.74 g of PEG8-(OMs)2 in 12 ml of tetrahydrofuran were subsequently added. The temperature was raised to 60° C., reaction was carried out with stirring and monitored using TLC. After the reaction was completed, excess sodium hydride was quenched with water. The reaction solution was concentrated by rotary evaporation, the resulting residue was extracted with dichloromethane and water system, and the organic layer was separated. The organic layer was washed five times with a 5% aqueous sodium carbonate solution, separated and dried with anhydrous sodium sulfate. After the desiccant was removed, the organic layer was concentrated by rotary evaporation to obtain 4.07 g of residue. Then said residue was treated with 15 ml of hydrochloric acid (4.0 M) and stirred at room temperature overnight. After the reaction was completed, the pH of the reaction solution was adjusted to 3 to 5 with 4 M aqueous ammonia. Finally, chromatography purification was carried out to obtain product PEG8-(6-α-naltrexol)2-ether. The above-mentioned product was dissolved in 20 ml of ethanol, then 2.5 ml of hydrogen chloride ethanol solution (1.0 M) was added, and the mixture was well mixed and then concentrated by rotary evaporation to obtain 1.0 g of residue. The resulting residue was dissolved in 20 ml of water and freeze-dried to obtain 0.84 g of almost white powdery solid, i.e. dihydrochloride salt of Na1029. 1H-NMR (400 MHz, D2O), δ ppm 6.72-6.77 (2H, d, J=8.0 Hz), 6.62-6.68 (2H, d, J=8.0 Hz), 4.81-4.88 (2H, d, J=4.8 Hz), 3.90-4.02 (4H, m), 3.66-3.74 (2H, m), 3.44-3.66 (30H, m), 3.24-3.34 (2H, d, J=20.0 Hz), 3.16-3.24 (2H, m), 3.03-3.14 (4H, m), 2.86-2.97 (2H, m), 2.72-2.84 (2H, m), 2.35-2.47 (2H), 1.68-1.79 (2H, m), 0.47-1.68 (6H, m), 1.16-1.30 (2H, m), 0.91-1.04 (2H, m), 0.67-0.77 (2H, m), 0.57-0.67 (2H, m), 0.28-0.43 (4H, m) LC/MS (ESI) m/z 1022.2 [M+H]+ and 511.9 [M+2H]++.

Na1033: Under the protection of argon, 0.92 g of sodium hydride and 20 ml of dimethylformamide were added to a reaction flask and stirred to be a suspension. Then, 3.00 g of 3-MOM-6-α-naltrexol in 12 ml of tetrahydrofuran and 2.00 g of PEG10-(OMs)2 in 12 ml of tetrahydrofuran were subsequently added. The temperature was raised to 60° C., reaction was carried out with stirring and monitored using TLC. After the reaction was completed, excess sodium hydride was quenched with water. The reaction solution was concentrated by rotary evaporation, the resulting residue was extracted with dichloromethane and water system, and the organic layer was separated. The organic layer was washed five times with a 5% aqueous sodium carbonate solution, separated and dried with anhydrous sodium sulfate. After the desiccant was removed, the organic layer was concentrated by rotary evaporation to obtain 4.18 g of residue. Then said residue was treated with 15 ml of hydrochloric acid (4.0 M) and stirred at room temperature overnight. After the reaction was completed, the pH of the reaction solution was adjusted to 3 to 5 with 4 M aqueous ammonia. Finally, chromatography purification was carried out to obtain product PEG10-(6-α-naltrexol)2-ether. The above-mentioned product was dissolved in 20 ml of ethanol, then 2.5 ml of hydrogen chloride—ethanol solution (1.0 M) was added, and the mixture was well mixed then and concentrated by rotary evaporation to obtain 1.3 g of residue. The resulting residue was dissolved in 20 ml of water and freeze-dried to obtain 1.00 g of almost white powdery solid, i.e. dihydrochloride salt of Na1033. 1 H-NMR (400 MHz, D2O), δ ppm 6.72-6.77 (2H, d, J=8.0 Hz), 6.62-6.68 (2H, d, J=8.0 Hz), 4.81-4.88 (2H, d, J=4.8 Hz), 3.90-4.02 (4H, m), 3.67-3.74 (2H, m), 3.44-3.67 (38H, m), 3.24-3.34 (2H, d, J=20.0 Hz), 3.16-3.24 (2H, m), 3.03-3.14 (4H, m), 2.86-2.97 (2H, m), 2.72-2.84 (2H, m), 2.35-2.47 (2H, m), 1.68-1.79 (2H, m), 1.47-1.68 (6H, m), 1.16-1.30 (2H, m), 0.91-1.04 (2H, m), 0.67-0.77 (2H, m), 0.57-0.67 (2H, m), 0.28-0.43 (4H, m). LC/MS (ESI) m/z 1110.2 [M+H]+ and 555.9 [M+2H]++.

Na1022: Under the protection of argon, 1.05 g of sodium hydride and 20 ml of dimethylformamide were added to a reaction flask and stirred to be a suspension. Then, 2.70 g of 3-MOM-6-β-naltrexol in 12 ml of tetrahydrofuran and 1.25 g of PEG4-(OMs)2 in 12 ml of tetrahydrofuran were subsequently added. The temperature was raised to 60° C., reaction was carried out with stirring and monitored using TLC. After the reaction was completed, excess sodium hydride was quenched with water. The reaction solution was concentrated by rotary evaporation, the resulting residue was extracted with dichloromethane and water system, and the organic layer was separated. The organic layer was washed five times with a 5% aqueous sodium carbonate solution, separated and dried with anhydrous sodium sulfate. After the desiccant was removed, the organic layer was concentrated by rotary evaporation to obtain 3.05 g of residue. Then the resulting residue was treated with 15 ml of hydrochloric acid (4.0 M) and stirred at room temperature overnight. After the reaction was completed, the pH of the reaction solution was adjusted to 3 to 5 with 4 M aqueous ammonia. Finally, chromatography purification was carried out to obtain product PEG4-(6-β-naltrexol)2-ether. The above-mentioned product was dissolved in 20 ml of ethanol, then 2.5 ml of hydrogen chloride—ethanol solution (1.0 M) was added, and the mixture was well mixed and then concentrated by rotary evaporation to obtain 0.96 g of residue. The resulting residue was dissolved in 20 ml of water and freeze-dried to obtain 0.56 g of almost white powdery solid, i.e. dihydrochloride salt of Na1022. 1H-NMR (400 MHz, D2O), δ ppm 6.69-6.74 (2H, d, J=8.0 Hz), 6.63-6.69 (2H, d, 0.1=8.0 Hz), 4.49-4.56 (2H, d, J=6.4 Hz), 3.90-3.96 (2H, d, J=5.6 Hz), 3.64-3.71 (4H, m), 3.48-3.63 (12H, m), 3.18-3.32 (6H, m), 2.99-3.11 (4H, m), 2.78-2.88 (2H, m), 2.54-2.68 (2H, m), 2.28-2.41 (2H, m), 1.73-1.85 (2H, m), 1.59-1.70 (4H, m), 1.46-1.59 (2H, m), 1.30-1.44 (2H, m), 0.88-1.02 (2H, m), 0.64-0.75 (2H, m), 0.54-0.64 (2H, m), 0.25-0.41 (4H, m). LC/MS (ESI) m/z 845.8 [M+H]+ and 423.9 [M+2H]++.

Na1026: Under the protection of argon, 1.10 g of sodium hydride and 20 ml of dimethylformamide were added to a reaction flask and stirred to be a suspension. Then, 2.80 g of 3-MOM-6-β-naltrexol in 12 ml of tetrahydrofuran and 1.36 g of PEG6-(OMs)2 in 12 ml of tetrahydrofuran were subsequently added. The temperature was raised to 60° C., reaction was carried out with stirring and monitored using TLC. After the reaction was completed, excess sodium hydride was quenched with water. The reaction solution was concentrated by rotary, evaporation, the resulting residue was extracted with dichloromethane and water system, and the organic layer was separated. The organic layer was washed five times with a 5% aqueous sodium carbonate solution, separated and dried with anhydrous sodium sulfate. After the desiccant was removed, the organic layer was concentrated by rotary evaporation to obtain 3.60 g of residue. Then the resulting residue was treated with 15 ml of hydrochloric acid (4.0 M) and stirred at room temperature overnight. After the reaction was completed, the pH of the reaction solution was adjusted to 3 to 5 with 4 M aqueous ammonia. Finally, chromatography purification was carried out to obtain product PEG6-(6-β-naltrexol)2-ether. The above-mentioned product was dissolved in 20 ml of ethanol, then 2.5 ml of hydrogen chloride ethanol solution (1.0 M) was added, and the mixture was well mixed and then concentrated by rotary evaporation to obtain 1.05 g of residue. The resulting residue was dissolved in 20 ml of water and freeze-dried to obtain 0.61 g of almost white powdery solid, i.e. dihydrochloride salt of Na1026. 1H-NMR (400 MHz, D2O), δ ppm 6.73-6.78 (2H, d, J=8.4 Hz), 6.67-6.72 (2H, d, J=8.0 Hz), 4.52-4.58 (2H, d, J=6.4 Hz), 3.92-3.99 (2H, d, J=6.0 Hz), 3.66-3.74 (4H, m), 3.50-3.65 (20H, m), 3.20-3.34 (6H, m), 3.02-3.15 (4H, m), 2.81-2.91 (2H, m), 2.57-2.71 (2H, m), 2.31-2.45 (2H, m), 1.76-1.88 (2H, m), 1.61-1.73 (4H, m), 1.51-1.62 (2H, m), 1.34-1.48 (2H, m), 0.91-1.04 (2H, m), 0.67-0.77 (2H, m), 0.57-0.67 (2H, m), 0.28-0.43 (4H, m). LC/MS (ESI) m/z 934.1 [M+H]+ and 467.8 [M+2H]++.

Na1030: Under the protection of argon, 1.10 g of sodium hydride and 20 ml of dimethylformamide were added to a reaction flask and stirred to be a suspension. Then, 2.8 g of 3-MOM-6-β-naltrexol in 12 ml of tetrahydrofuran and 1.45 g of PEG8-(OMs)2 in 12 ml of tetrahydrofuran were subsequently added. The temperature was raised to 60° C., reaction was carried out with stirring and monitored using TLC. After the reaction was completed, excess sodium hydride was quenched with water. The reaction solution was concentrated by rotary evaporation, the resulting residue was extracted with dichloromethane and water system, and the organic layer was separated. The organic layer was washed five times with a 5% aqueous sodium carbonate solution, separated and dried with anhydrous sodium sulfate. After the desiccant was removed, the organic layer was concentrated by rotary evaporation to obtain 3.80 g of residue. Then the resulting residue was treated with 15 ml of hydrochloric acid (4.0 M) and stirred at room temperature overnight. After the reaction was completed, the pH of the reaction solution was adjusted to 3 to 5 with 4 M aqueous ammonia. Finally, chromatography purification was carried out to obtain product PEG8-(6-β-naltrexol)2-ether. The above-mentioned product was dissolved in 20 ml of ethanol, then 2.5 ml of hydrogen chloride—ethanol solution (1.0 M) was added, and the mixture was well mixed and then concentrated by rotary evaporation to obtain 1.0 g of residue. The resulting residue was dissolved in 20 ml of water and freeze-dried to obtain 0.51 g of almost white powdery solid, i.e. dihydrochloride salt of Na1030. 1H-NMR (400 MHz, D2O), δ ppm 6.71-6.77 (2H, d, J=8.0 Hz), 6.65-6.71 (2H, d, J=8.0 Hz), 4.50-4.56 (2H, d, J=6.4 Hz)), 3.91-3.97 (2H, d, J=6.0 Hz), 3.64-3.71 (4H, m), 3.48-3.63 (28H, m), 3.18-3.32 (6H, m), 2.99-3.11 (4H, m), 2.78-2.88 (2H, m), 2.54-2.68 (2H, m), 2.28-2.41 (2H, m), 1.73-1.85 (2H, m), 1.59-1.70 (4H, m), 1.48-1.59 (2H, m), 1.32-1.44 (2H, m), 0.88-1.02 (2H, m), 0.64-0.75 (2H, m), 0.54-0.64 (2H, m), 0.25-0.41 (4H, m). LC/MS (ESI) m/z 512.0 [M+2H]++.

Na1037: Under the protection of argon, 0.37 g of sodium hydride and 20 ml of dimethylformamide were added to a reaction flask and stirred to be a suspension. Then, 0.92 g of 3-MOM-6-α-naltrexol in 12 ml of tetrahydrofuran and 0.823 g of mPEG6-OMs in 12 ml of tetrahydrofuran were subsequently added. The temperature was raised to 60° C., reaction was carried out with stirring and monitored using TLC. After the reaction was completed, excess sodium hydride was quenched with water. The reaction solution was concentrated by rotary evaporation, the resulting residue was extracted with dichloromethane and water system, and the organic layer was separated. The organic layer was washed five times with a 5% aqueous sodium carbonate solution, separated and dried with anhydrous sodium sulfate. After the desiccant was removed, the organic layer was concentrated by rotary evaporation to obtain 1.64 g of residue. Then the resulting residue was treated with 15 ml of hydrochloric acid (4.0 M) and stirred at room temperature overnight. After the reaction was completed, the pH of the reaction solution was adjusted to 3 to 5 with 4 M aqueous ammonia. Finally, chromatography purification was carried out to obtain product mPEG6-(6-α-naltrexol)-ether. The above-mentioned product was dissolved in 20 ml of ethanol, then 3.5 ml of hydrogen chloride ethanol solution (1.0 M) was added, and the mixture was well mixed and then concentrated by rotary evaporation to obtain 0.65 g of residue. Said residue was dissolved in 20 ml of water and freeze-dried to obtain 0.42 g of almost white powdery solid, i.e. hydrochloride salt of Na1037. 1H-NMR (400 MHz, D2O), δ ppm 6.72-6.78 (1H, d, J=8.0 Hz), 6.62-6.69 (1H, d, J=8.4 Hz), 4.82-4.88 (1H, d, J=4.8 Hz), 3.91-4.01 (2H, m), 3.67-3.75 (1H, m), 3.43-3.67 (23H, m), 3.16-3.34 (5H, m), 3.03-3.15 (2H, m), 2.86-2.97 (1H, m), 2.72-2.85 (1H, m), 2.35-2.48 (1H, m), 1.70-1.82 (1H, m), 1.48-1.70 (3H, m), 1.20-1.35 (1H, m), 0.91-1.04 (1H, m), 0.67-0.77 (1H, m), 0.57-0.67 (1H, m), 0.28-0.43 (2H, m). LC/MS (ESI) m/z 623.1 [M+H]+.

Na1041: Under the protection of argon, 0.44 g of sodium hydride and 20 ml of dimethylformamide were added to a reaction flask and stirred to be a suspension. Then, 1.00 g of 3-MOM-6-α-naltrexol in 12 ml of tetrahydrofuran and 1.05 g of mPEG8-OMs in 12 ml of tetrahydrofuran were subsequently added. The temperature was raised to 60° C., reaction was carried out with stirring and monitored using TLC. After the reaction was completed, excess sodium hydride was quenched with water. The reaction solution was concentrated by rotary evaporation, the resulting residue was extracted with dichloromethane and water system, and the organic layer was separated. The organic layer was washed five times with a 5% aqueous sodium carbonate solution, separated and dried with anhydrous sodium sulfate, After the desiccant was removed, the organic layer was concentrated by rotary evaporation to obtain 1.76 g of residue. Then the resulting residue was treated with 15 ml of hydrochloric acid (4.0 M) and stirred at room temperature overnight. After the reaction was completed, the pH of the reaction solution was adjusted to 3 to 5 with 4 M aqueous ammonia. Finally, chromatography purification was carried out to obtain product mPEG8-(6-α-naltrexol)-ether. The above-mentioned product was dissolved in 20 ml of ethanol, then 3.0 ml of hydrogen chloride—ethanol solution (1.0 M) was added, and the mixture was well mixed and then concentrated by rotary evaporation to obtain 0.95 g of residue. The resulting residue was dissolved in 20 ml of water and freeze-dried to obtain 0.67 g of almost white powdery solid, i.e. hydrochloride salt of Na1041. 1H-NMR (400 MHz, D2O), δ ppm 6.72-6.78 (1H, d, J=8.0 Hz), 6.62-6.69 (1H, d, J=8.4 Hz), 4.82-4.88 (1H, d, J=4.8 Hz), 3.91-4.01 (2H, m), 3.67-3.75 (1E, m), 3.43-3.67 (31H, m), 3.16-3.34 (51-1, in), 3.03-3.15 (2H, m), 2.86-2.97 (1H, m), 2.72-2.85 (1H, m), 2.35-2.48 (1H, m), 1.70-1.82 (1H, m), 1.48- 1.70 (3H, m), 1.20-1.35 (1H, m), 0.91-1.04 (1H, m) 0.67-0.77 (1H, m), 0.57-0.67 (1H, m), 0.28-0.43 (2H, m). LC/MS (ESI) m/z 711.1 [M+H]+.

Na1038: Under the protection of argon, 0.55 g of sodium hydride and 20 ml of dimethylformamide were added to a reaction flask and stirred to be a suspension. Then, 1.20 g of 3-MOM-6-β-naltrexol in 12 ml of tetrahydrofuran and 1.05 g of mPEG6-OMs in 12 ml of tetrahydrofuran were subsequently added. The temperature was raised to 60° C., reaction was carried out with stirring and monitored using TLC. After the reaction was completed, excess sodium hydride was quenched with water. The reaction solution was concentrated by rotary, evaporation, the resulting residue was extracted with dichloromethane and water system, and the organic layer was separated. The organic layer was washed five times with a 5% aqueous sodium carbonate solution, separated and dried with anhydrous sodium sulfate. After the desiccant was removed and concentrated by rotary evaporation to obtain 1.90 g of residue. Then the resulting residue was treated with 15 ml of hydrochloric acid (4.0 M) and stirred at room temperature overnight. After the reaction was completed, the pH of the reaction solution was adjusted to 3 to 5 with 4 M aqueous ammonia. Finally, chromatography purification was carried out to obtain product mPEG6-(6-β-naltrexol)-ether. The above-mentioned product was dissolved in 20 ml of ethanol, then 2.5 ml of hydrogen chloride—ethanol solution (1.0 M) was added, and the mixture was well mixed and then concentrated by rotary evaporation to obtain 1.0 g of residue. Said residue was dissolved in 20 ml of water and freeze-dried to obtain 0.71 g of almost white powdery solid, i.e. hydrochloride salt of Na1038. 1H-NMR (400 MHz, D2O), δ ppm 6.75-6.80 (1H, d, J=8.0 Hz), 6.68-6.75 (1H, d, J=8.4 Hz), 4.52-4.60 (1H, d, J=6.4 Hz), 3.92-4.01 (1H, d, J=6.0 Hz), 3.68-3.76 (2H, t), 3.54-3.67 (20H, m), 3.47-3.54 (2H, m), 3.20-3.36 (6H, m), 3.02-3.17 (2H, m), 2.81-2.91 (1H, m), 2.59-2.73 (1H, m), 2.32-2.46 (1H, m), 1.78-1.89 (1H, m), 1.52-1.74 (3H, m), 1.36-1.50 (1H, m), 0.91-1.04 (1H, m), 0.67-0.77 (1H, m), 0.57-0.67 (1H, m) 0.28-0.43 (2H, m) LC/MS (ESI) m/z 623.1 [M+H]+.

Na1045: Under the protection of argon, 0.60 g of sodium hydride and 20 ml of dimethylformamide were added to a reaction flask and stirred to be a suspension. Then, 1.40 g of 3-MOM-6-α-naloxol in 12 ml of tetrahydrofuran and 1.38 g of mPEG6-OMs in 12 ml of tetrahydrofuran were subsequently added. The temperature was raised to 60° C., reaction was carried out with stirring and monitored using TLC. After the reaction was completed, excess sodium hydride was quenched with water. The reaction solution was concentrated by rotary evaporation, the resulting residue was extracted with dichloromethane and water system, and the organic layer was separated. The organic layer was washed five times with a 5% aqueous sodium carbonate solution, separated and dried with anhydrous sodium sulfate. After the desiccant was removed and concentrated by rotary evaporation to obtain 2.47 g of residue. Then the resulting residue was treated with 15 ml of hydrochloric acid (4.0 M) and stirred at room temperature overnight. After the reaction was completed, the pH of the reaction solution was adjusted to 3 to 5 with 4 M aqueous ammonia. Finally, chromatography purification was carried out to obtain product mPEG6-(6-α-naloxol)-ether. The above-mentioned product was dissolved in 20 ml of ethanol; then 2.5 ml of hydrogen chloride—ethanol solution (1.0 M) was added, and the mixture was well mixed and then concentrated by rotary evaporation to obtain 1.5 g of residue. The resulting residue was dissolved in 20 ml of water and freeze-dried to obtain 1.11 g of almost white powdery solid, i.e. hydrochloride salt of Na1045. 1H-NMR (400 MHz, D2O), δ ppm 6.72-6.79 (1H, d, J=8.4 Hz), 6.62-6.70 (1H, d, J=8.0 Hz), 5.72-5.88 (1H, m), 5.48-5.60 (2H, t), 4.81-4.88 (1H, d, J=5.2 Hz), 3.89-3.99 (1H, m), 3.40-3.85 (27H, m), 3.27-3.37 (1H, d, J=20.0 Hz)), 3.28 (3H, s), 3.10-3.21 (1H, m) 2.95-3.08 (1H, m), 2.76-2.90 (1H, m), 2.34-2.48 (1H, m), 1.62-1.80 (2H m), 1.45-1.62 (2H, m), 1.21-1.35 (1H, m). LC/MS (ESI) m/z 609.1 [M+H]+.

Na1049: Under the protection of argon, 0.60 g of sodium hydride and 20 ml of dimethylformamide were added to a reaction flask and stirred to be a suspension. Then, 1.50 g of 3-MOM-6-α-naloxol in 12 ml of tetrahydrofuran and 1.81 g of mPEG8-OMs in 12 ml of tetrahydrofuran were subsequently added. The temperature was raised to 60° C., reaction was carried out with stirring and monitored using TLC. After the reaction was completed, excess sodium hydride was quenched with water. The reaction solution was concentrated by rotary evaporation, the resulting residue was extracted with dichloromethane and water system, and the organic layer was separated. The organic layer was washed five times with a 5% aqueous sodium carbonate solution, separated and dried with anhydrous sodium sulfate. After the desiccant was removed, the organic layer was concentrated by rotary evaporation to obtain 2.93 g of residue. Then the resulting residue was treated with 15 ml of hydrochloric acid (4.0 M) and stirred at room temperature overnight. After the reaction was completed, the pH of the reaction solution was adjusted to 3 to 5 with 4 M aqueous ammonia. Finally, chromatography purification was carried out to obtain product mPEG8-(6-α-naloxol)-ether. The above-mentioned product was dissolved in 20 ml of ethanol, the pH was adjusted to 1 to 2 with hydrogen chloride—ethanol solution (1.0 M), and the mixture was well mixed and then concentrated by rotary evaporation to obtain 1.6 g of residue. Said residue was dissolved in 20 ml of water and freeze-dried to obtain 1.33 g of almost white powdery solid, i.e. hydrochloride salt of Na1049. 1H-NMR (400 MHz, D2O), δ ppm 6.72-6.79 (1H, d, J=8.4 Hz), 6.62-6.70 (1H, d, J=8.4 Hz), 5.72-5.88 (1H, m), 5.48-5.60 (2H, t), 4.81-4.88 (1H, d, J=5.2 Hz), 3.89-3.99 (1H, m), 3.40-3.85 (35H, m), 3.27-3.37 (1H, d, J=20.0 Hz)), 3.28 (3H, s), 3.10-3.21 (1H, m), 2.95-3.08 (1H, m), 2.76-2.90 (1H, m), 2.34-2.48 (1H, m), 1.62-1.80 (2H, m), 1.45-1.62 (2H, m), 1.21-1.35 (1H, m). LC/MS (ESI) m/z 697.1 [M+H]+.

Na1046: Under the protection of argon, 0.55 g of sodium hydride and 20 ml of dimethylformamide were added to a reaction flask and stirred to be a suspension. Then, 1.26 g of 3-MOM-6-β-naloxol in 12 ml of tetrahydrofuran and 1.24 g of mPEG6-OMs in 12 ml of tetrahydrofuran were subsequently added. The temperature was raised to 60° C., reaction was carried out with stirring and monitored using TLC. After the reaction was completed, excess sodium hydride was quenched with water. The reaction solution was concentrated by rotary evaporation, the resulting residue was extracted with dichloromethane and water system, and the organic layer was separated. The organic layer was washed five times with a 5% aqueous sodium carbonate solution, separated and dried with anhydrous sodium sulfate. After the desiccant was removed and concentrated by rotary evaporation to obtain 2.08 g of residue. Then the resulting residue was treated with 15 ml of hydrochloric acid (4.0 M) and stirred at room temperature overnight. After the reaction was completed, the pH of the reaction solution was adjusted to 3 to 5 with 4 M aqueous ammonia. Finally, chromatography purification was carried out to obtain product mPEG6-(6-β-naloxol)-ether. The above-mentioned product was dissolved in 20 ml of ethanol, then 2.5 ml of hydrogen chloride—ethanol solution (1.0 M) was added, and the mixture was well mixed and then concentrated by rotary evaporation to obtain 1.1 g of residue. Said residue was dissolved in 20 ml of water and freeze-dried to obtain 0.85 g of almost white powdery solid, i.e. hydrochloride salt of Nal046. 1H-NMR (400 MHz, D2O), δ ppm 6.75-6.81 (1H, d, 0.1=8.0 Hz), 6.69-6.75 (1H, d, J=8.4 Hz), 5.73-5.88 (1H, m), 5.49-5.59 (2H, m), 4.52-4.59 (1H, d, J=6.8 Hz), 3.45-3.85 (27H, m), 3.23-3.37 (5H, m), 3.10-3.20 (1H, m), 2.96-3.08 (1H, m), 2.62-2.76 (1H, m), 2.32-2.45 (1H, m), 1.76-1.88 (1H, m), 1.54-1.72 (3H, m), 1.33-1.47 (1H, m) LC/MS (ESI) m/z 609.2 [M+H]+.

Example 6: In Vitro Activity Test

CHO-K1/Gα15/OPRM1 cells (Gen Script (Nanjing) Co., Ltd.) stably expressing OPRM1 (Mµ opioid receptor gene) receptor were cultured in 10-cm dishes at 37° C./5% $CO_2$ incubator. When the cell reached 80% to 85% confluence, cells were digested and collected. Cell suspension was inoculated into a 384-well microplate at a density of 15,000 cells per well, and cultured in a 37° C./5% $CO_2$ incubator for at least 18 hours before experiment.

Before the test, the conjugates to be tested was diluted with HBSS buffer (containing 20 mM HEPES) and prepared as 5× solution with a concentration five times of the test solution. The final concentrations of the conjugate were 0.128 nM, 0.64 nM, 3.2 nM, 1.6 nM, 80 nM, 400 nM, 2000 mM and 10000 nM, each in duplicate. The concentration of the corresponding control DMSO is 0.1%.

The protocol for preparing agonist detection: cells were inoculated into 384-well microplates, 20 µl of cell suspension per well (containing 15,000 cells); the plate was placed in 37° C./5% $CO_2$ incubator to continue the culture; cells were taken out after 18 hours, and dye was added, 20 µl per well; the plate was incubated in 37° C./5% $CO_2$ incubator for 1 hour and equilibrated at room temperature for 15 minutes; and 10 µl of 5× test solution of agonist was added to each well for RFU value detection.

The protocol for preparing inhibitor detection: cells were inoculated into 384-well microplates, 20 µl of cell suspension per well (containing 15,000 cells); the plate was placed in 37° C./5% $CO_2$ incubator to continue the culture; cells were taken out after 18 hours; for the inhibitor detection, 20 µl of dye was added to the plate, and then 10 µl of prepared conjugate solution was added; the plate was incubated in 37° C./5% $CO_2$ for 1 hour and equilibrate at room temperature for 15 minutes; 12.5 µl of 5× EC80 positive agonist was added for RFU value detection.

The 384-well microplate containing the conjugate solution (5× test concentration), cell plate and pipette tip box were placed in FLIPR (Molecule Devices), and the agonist detection program was run. The overall detection time of the instrument was 120 seconds. 10 µl of agonist was automatically added to the plate at the $21^{st}$ second. The 384-well microplate containing 5× EC80 positive agonist, cell plate and pipette tip box were placed in FLIPRTETRA (Molecule Devices), and the inhibitor detection program was run. The overall detection time of the instrument was 120 seconds. 12.5 µl of positive agonist was automatically added to the plate at the $21^{st}$ second. The effects of 13 conjugates on the OPRM1 receptor were shown in Table 4 below

TABLE 4

IC50 of the conjugates of the present disclosure

| Name | IC50(M) | Highest concentration | Inhibition rate (%) of highest concentration (mean ± standard deviation) (N = 2) |
|---|---|---|---|
| Naltrexone hydrochloride | 4.15 × 10−8 | 10000 nM | 101.35 ± 0.65 |
| Naloxone hydrochloride | 9.75 × 10−8 | 10000 nM | 100.08 ± 0.40 |
| Nal053 | 2.50 × 10−7 | 10000 nM | 101.85 ± 0.97 |
| Nal021 | 2.29 × 10−7 | 10000 nM | 100.31 ± 0.56 |
| Nal025 | 1.85 × 10−7 | 10000 nM | 100.63 ± 0.48 |
| Nal026 | 1.83 × 10−7 | 10000 nM | 100.52 ± 0.26 |
| Nal029 | 1.61 × 10−7 | 10000 nM | 98.00 ± 3.09 |
| Nal033 | 1.97 × 10−7 | 10000 nM | 99.12 ± 1.00 |
| Nal037 | 2.25 × 10−7 | 10000 nM | 100.58 ± 0.34 |
| Nal041 | 2.10 × 10−7 | 10000 nM | 95.82 ± 1.86 |
| Nal045 | 1.32 × 10−6 | 10000 nM | 90.44 ± 3.22 |
| Nal046 | 3.84 × 10−6 | 10000 nM | 79.55 ± 5.73 |
| Nal049 | 1.05 × 10−6 | 10000 nM | 94.31 ± 5.39 |

The data in the above table shows that the conjugates with two naltrexone and PEG (i.e., Nal053, Nal021, Nal025, Nal026, Nal029, and Nal033) exhibit a lower IC50 than the naloxone-PEG conjugate or the mononaltrexone-PEG conjugate; when the number of the repeating units of polyethylene glycol is a specific value (e.g., 6, 8, 10), the conjugates of the present disclosure exhibits even lower IC50, which is really unexpected.

Example 7: Experimental Study Regarding the Blood-Brain Barrier

The experimental study on whether the conjugate test group can pass through the blood-brain barrier was completed by using the mouse hot plate analgesia experiment. Morphine has an analgesic effect, and if the conjugate to be tested can antagonize the analgesic effect of morphine, then it can be concluded that the conjugate can pass through the blood-brain barrier.

Six conjugates Nal021, Nal029, Nal045, Nal037, Nal041, and Nal049 were subjected to mouse hot plate analgesia experiments for four times, respectively. In each experiment, mice (JOINN Laboratories (Suzhou)) were randomly divided into four groups (eight per group): one blank control group, one morphine control group, and two other groups which were administered with morphine by gavage first, and then low dose and high dose of the conjugates were subcutaneously injected respectively. The mice were put on a hot plate (55±0.1) ° C. before administration, and the time was recorded immediately. The duration from the beginning on the hot plate to the first hind paw licking was recorded as the reaction time of heat-pain sensation (i.e., pain threshold, the unit is second (s)). The pain threshold was set as 100% analgesia if there was no hind paw licking in 60 seconds. It was recorded as 60 seconds when the time exceeded 60 seconds to prevent burn of foot. The mice were again put on a (55±0.1) ° C. hot plate 60 minutes after the administration of drug and the reaction time of heat-pain sensation was recorded. The experimental result was shown in the table below. It can be seen that the difference between the pain threshold before and after administration in the blank control group is not significant (P>0.05), while the pain threshold before and after administration in the morphine control group are significantly different (P<0.01), and the differences between the pain thresholds before and after administration in high-dose groups of Na1037 and Na1041 are not significant (P>0.05). The pain threshold before and after administration in each other drug-administered groups is significantly different (P<0.05). Therefore, it can be concluded that the conjugates Na1037 and Na1041 can pass through the blood-brain barrier so as to antagonize the analgesic effect of morphine. Na1021, Na1029, Na1045, or Na1049 cannot pass through the blood-brain barrier. The value of the pain thresholds before and after administration was compared and the percentage of increase in pain threshold was calculated according to the following formula to determine the effect of drug on antagonizing morphine analgesia.

Percentage of increase in pain threshold=[(average heat pain threshold after administration−average pain threshold before administration)/average pain threshold before administration]×100%

TABLE 5

Experimental Result of Hot Plate Analgesia Experiment with Nal021 and Nal029

| Group | Method of Treatment | Average Pain Threshold before Administration (s) Mean ± SD | Average Pain Threshold after Administration (s) Mean ± SD |
|---|---|---|---|
| 1 | Blank Control | 25.00 ± 10.54 | 31.13 ± 13.85 |
| 2 | Morphine Control | 19.25 ± 5.57 | 53.25 ± 10.96** |
| 3 | NAL021 (4.36 μmol/kg) + Morphine | 20.63 ± 7.07 | 56.25 ± 10.61** |
| 4 | NAL021 (21.8 μmol/kg) + Morphine | 18.63 ± 4.60 | 59.75 ± 0.71** |
| 5 | NAL029 (3.66 μmol/kg) + Morphine | 20.00 ± 5.71 | 60.00 ± 0** |
| 6 | NAL029 (18.28 μmol/kg) + Morphine | 22.13 ± 7.26 | 56.5 ± 9.90** |

Note:
* P < 0.05,
**P < 0.01

TABLE 6

Experimental Result of Hot Plate Analgesia Experiment with Nal045

| Group | Method of Treatment | Average Pain Threshold before Administration (s) Mean ± SD | Average Pain Threshold after Administration (s) Mean ± SD |
|---|---|---|---|
| 1 | Blank Control | 21.38 ± 5.13 | 25.00 ± 5.81 |
| 2 | Morphine Control | 20.38 ± 3.93 | 52.00 ± 9.67** |
| 5 | NAL045 (3.10 μmol/kg) + Morphine | 20.38 ± 4.53 | 52.13 ± 14.78** |

TABLE 6-continued

Experimental Result of Hot Plate Analgesia Experiment with Nal045

| Group | Method of Treatment | Average Pain Threshold before Administration (s) Mean ± SD | Average Pain Threshold after Administration (s) Mean ± SD |
|---|---|---|---|
| 6 | NAL045 (15.52 μmol/kg) + Morphine | 24.00 ± 8.38 | 51.00 ± 11.43** |

Note:
* P < 0.05,
**P < 0.01

TABLE 7

Experimental Result of Hot Plate Analgesia Experiment with Nal037

| Group | Method of Treatment | Average Pain Threshold before Administration (s) Mean ± SD | Average Pain Threshold after Administration (s) Mean ± SD |
|---|---|---|---|
| 1 | Blank Control | 21.13 ± 4.26 | 20.75 ± 7.25 |
| 2 | Morphine Control | 20.88 ± 4.91 | 38.5 ± 15.58** |
| 5 | Nal037 (4 μmol/kg) + Morphine | 19.38 ± 5.21 | 31.50 ± 11.83* |
| 6 | Nal037 (20 μmol/kg) + Morphine | 20.5 ± 3.93 | 20.88 ± 5.87 |

Note:
*P < 0.05,
**P < 0.01

TABLE 8

Experimental Result of Hot Plate Analgesia Experiment with Nal041 and Nal049

| Group | Method of Treatment | Average Pain Threshold before Administration (s) Mean ± SD | Average Pain Threshold after Administration (s) Mean ± SD |
|---|---|---|---|
| 1 | Blank Control | 17.50 ± 3.59 | 21.87 ± 5.84 |
| 2 | Morphine Control | 15.12 ± 6.38 | 39.00 ± 17.25** |
| 3 | Nal041 (4 μmol/kg) + Morphine | 14.25 ± 1.75 | 38.5 ± 14.74** |
| 4 | Nal041 (20 μmol/kg) + Morphine | 16.88 ± 6.79 | 22.00 ± 5.12 |
| 5 | Nal049 (4 μmol/kg) + Morphine | 14.00 ± 7.09 | 31.63 ± 10.04** |
| 6 | Nal049 (20 μmol/kg) + Morphine | 13.5 ± 5.07 | 25.88 ± 7.64** |

Note:
* P < 0.05,
**P < 0.01

TABLE 9

Percentage of Increase in Pain Threshold for Each Compound

| Serial number | Group with Different dose of Each Compound | Percentage of Increase in Pain Threshold |
|---|---|---|
| 1 | NAL021 (4.36 μmol/kg) | 172.66% |
| 2 | NAL021 (21.8 μmol/kg) | 220.72% |
| 3 | NAL029 (3.66 μmol/kg) | 200.00% |
| 4 | NAL029 (18.28 μmol/kg) | 155.31% |
| 5 | NAL045 (3.10 μmol/kg) | 155.79% |

TABLE 9-continued

Percentage of Increase in Pain Threshold for Each Compound

| Serial number | Group with Different dose of Each Compound | Percentage of Increase in Pain Threshold |
|---|---|---|
| 6 | NAL045 (15.52 μmol/kg) | 112.50% |
| 7 | NAL037 (4 μmol/kg) | 62.54% |
| 8 | NAL037 (20 μmol/kg) | 1.85% |
| 9 | NAL041 (4 μmol/kg) | 170.18% |
| 10 | NAL041 (20 μmol/kg) | 30.33% |
| 11 | NAL049 (4 μmol/kg) | 125.93% |
| 12 | NAL049 (20 μmol/kg) | 91.70% |

Example 8: Experimental Study on Anti-Constipation

The anti-constipation study experiment was completed by using the test of antagonizing the antidiarrheal effect of loperamide hydrochloride. The specific experiment process was: the mice were divided into groups randomly, eight mice each group, wherein one group was administered with 0.5 mL of castor oil by gavage, one group was administered with 2 mg/kg loperamide hydrochloride and 0.5 mL of castor oil by gavage, and conjugate test groups were respectively administered with Na1021 (300 nmol/kg), Na1029 (300 nmol/kg), Na1033 (300 nmol/kg) and Na1045 (600 nmol/kg) by gavage first, and then with 2 mg/kg loperamide and 0.5 mL castor oil by gavage. The cumulative number of diarrhea times in the mice was observed in six hours after the administration, and the loose stools point was counted to determine diarrhea conditions. The result shows that the total number of diarrhea times in the castor oil control group is nearly two times as high as that compared with the loperamide hydrochloride castor oil control group six hours after the administration, indicating that the diarrhea model was effective. The total number of diarrhea times of Na1029 is relatively high six hours after the administration, and the anti-diarrhea effect of antagonizing loperamide hydrochloride is stronger, indicating that the anti-constipation is better. The specific data is shown in Table 10.

TABLE 10

Experimental Result for each Conjugate to Antagonize the Antidiarrheal Effect of Loperamide Hydrochloride

| Group | Method of Treatment | Total Number of Diarrhea Times Six Hours after Administration |
|---|---|---|
| 1 | Castor Oil Control | 16.625 ± 5.95 |
| 2 | Loperamide Hydrochloride + Castor Oil | 10.88 ± 7.14 |
| 4 | Na1029 (300 nmol/kg) + Loperamide Hydrochloride + Castor Oil | 20.88 ± 5.82 |
| 5 | Na1033 (300 nmol/kg) + Loperamide Hydrochloride + Castor Oil | 15.25 ± 4.13 |
| 6 | Na1045 (600 nmol/kg) + Loperamide Hydrochloride + Castor Oil | 9.75 ± 6.96 |

Example 9: Pharmacodynamical Experimental Study on Anti-Constipation of Conjugate Na1029

The mice were divided into groups randomly, eight mice each group, wherein one group was administered with 0.5 mL of castor oil by gavage, one group was administered with 2 mg/kg loperamide and 0.5 mL castor oil by gavage, other groups were respectively administered with different doses of conjugate Na1029 first, then with 2 mg/kg loperamide hydrochloride and 0.5 mL castor oil by gavage.

It can be seen from the experimental result that compared with the model control group, conjugate Na1029 can significantly antagonize the antidiarrheal effect of loperamide hydrochloride, and the pharmacodynamics is better than that of naltrexone with same dose and have a dose-dependent manner. The EC50 is 0.086 mg/kg approximately. The specific result is shown in Table 11 and FIG. 1.

TABLE 11

Experimental Result for Conjugate Na1029 to Antagonize Antidiarrheal Effect of Loperamide Hydrochloride

| Group | Method of Treatment | Total Number of Diarrhea Tinies Six Hours after Administration |
|---|---|---|
| 1 | Castor Oil Control | 11.13 ± 5.54 |
| 2 | Loperamide Hydrochloride + Castor Oil | 5.75 ± 3.69 |
| 3 | Na1029 (500 μg/kg) + Loperamide Hydrochloride + Castor Oil | 18.25 ± 3.99 |
| 4 | Na1029 (100 μg/kg) + Loperamide Hydrochloride + Castor Oil | 12.13 ± 5.67 |
| 5 | Na1029 (30 μg/kg) + Loperamide Hydrochloride + Castor Oil | 6.50 ± 5.88 |
| 6 | Na1029 (10 μg/kg) + Loperamide Hydrochloride + Castor Oil | 5.25 ± 7.42 |
| 7 | Naltrexone (500 μg/kg) + Loperamide Hydrochloride + Castor Oil | 14.00 ± 5.76 |

The above description is only preferred embodiments, which is only used as examples instead of a limitation to the combination of the features required to practice the present invention. The provided headings are not meant to limit the various embodiments of the present invention.

All publications and patents mentioned in this application are hereby incorporated by reference. Various modifications and variations of the described methods and compositions of the present disclosure are apparent to those having ordinary skill in the art without departing from the scope and spirit of the present invention. Although the present invention is described by way of specific preferred embodiments, it should be understood that the claimed invention should not be inappropriately limited to these specific embodiments. In fact, those various variations of the described modes for practicing the present invention that are obvious to those people having ordinary skill in the art are intended to be included within the protective scope of the appended claims.

What is claimed is:

1. A conjugate as represented by formula (V) or a pharmaceutically acceptable salt thereof: $W_1$—P—$W_2$ (V), wherein W₁ and W₂ each independently have structure of:

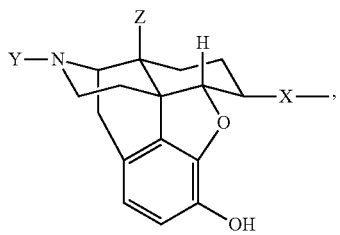

wherein
Y is

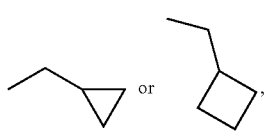 or ,

Z is —OH,
X is selected from the group consisting of amido group, amine group, carbamate group, thioether group, ether group, urea group and methylene group, and
P is a polyethylene glycol having 2 to 20 —CH₂CH₂O— structural unit.

2. The conjugate according to claim 1, wherein W₁ and W₂ are each independently:

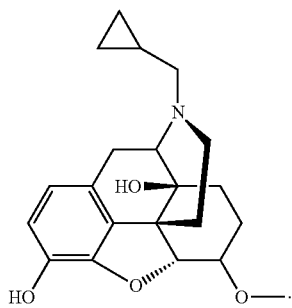

3. The conjugate according to claim 1, which is represented by formula (II) or a pharmaceutically acceptable salt thereof:

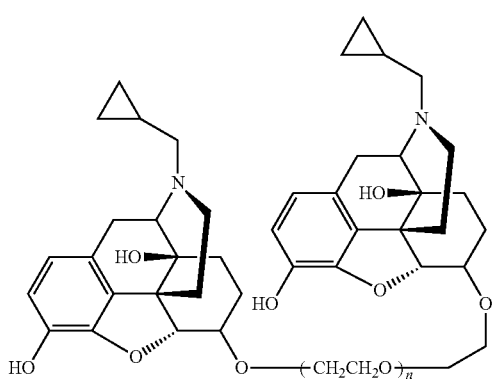

wherein, n is a natural number from 2 to 20.

4. The conjugate according to claim 1, which is represented by formula (III) or a pharmaceutically acceptable salt thereof:

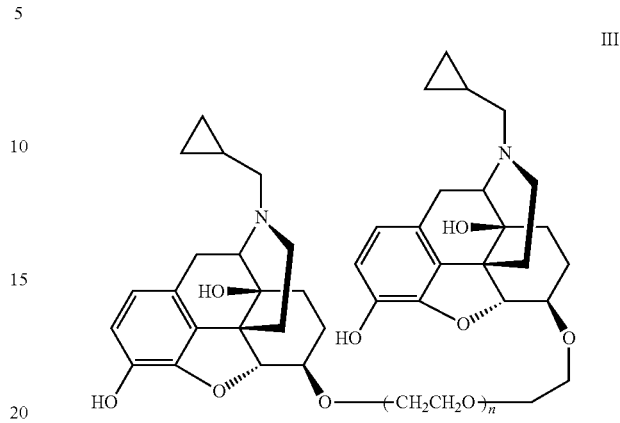

wherein, n is a natural number from 2 to 20.

5. The conjugate according to claim 1, which is represented by formula (IV) or a pharmaceutically acceptable salt thereof:

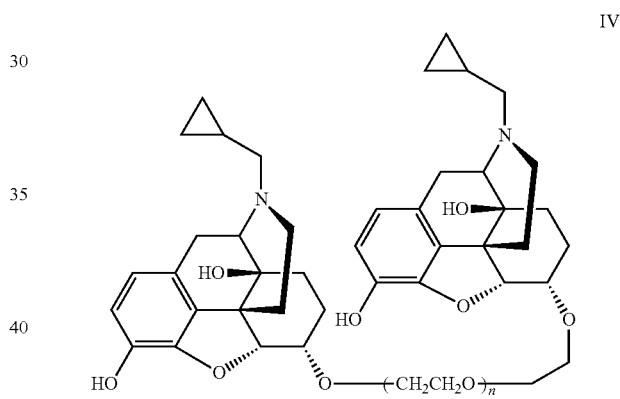

wherein, n is a natural number from 2 to 20.

6. The conjugate according to claim 3, wherein n is 3, 4, 6, 8, or 10.

7. The conjugate according to claim 1, wherein the hydrophilic polymer is a monodisperse polyethylene glycol having 2 to 10 —CH₂CH₂O— structural unit and the opioid receptor antagonist prior to conjugation is naltrexone.

8. The conjugate according to claim 1, which is selected from the group consisting of PEG3-(6-α-naltrexol)₂-ether, PEG4 (6-α-naltrexol)₂-ether, PEG6-(6-α-naltrexol)₂-ether, PEG8-(6-α-naltrexol)₂-ether, PEG10-(6-α-naltrexol)₂-ether, PEG4 (6-β-naltrexol)₂-ether, PEG6-(6-β-naltrexol)₂-ether, and PEG8-(6-β-naltrexol)₂-ether.

9. A pharmaceutical composition, comprising the conjugate according to claim 1, and a pharmaceutically acceptable carrier.

10. A kit, comprising the conjugate according to claim 1.

11. A method of treating constipation induced by opioid receptors, treating pain in combination with an opioid, reducing side effect caused by an opioid and preventing opioid abuse, comprising administrating an effective amount of the conjugate according to claim 1 to a subject in need thereof.

12. The conjugate according to claim 2, wherein $W_1$ and $W_2$ are each independently selected from the group consisting of
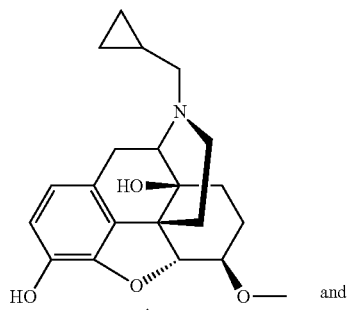 and
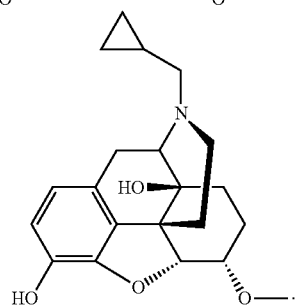
* * * * *